US008916579B2

(12) United States Patent
Boebel et al.

(10) Patent No.: US 8,916,579 B2
(45) Date of Patent: Dec. 23, 2014

(54) 5-FLUOROPYRIMIDINONE DERIVATIVES

(75) Inventors: Timothy A. Boebel, Indianapolis, IN (US); Kristy Bryan, Carmel, IN (US); Peter L. Johnson, Indianapolis, IN (US); Beth Lorsbach, Indianapolis, IN (US); Timothy P. Martin, Noblesville, IN (US); Kevin G. Meyer, Zionsville, IN (US); W. John Owen, Carmel, IN (US); Michael T. Sullenberger, Westfield, IN (US); Jeffery D. Webster, New Palestine, IN (US); Chenglin Yao, Westfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 325 days.

(21) Appl. No.: 12/851,272

(22) Filed: Aug. 5, 2010

(65) Prior Publication Data
US 2011/0053891 A1 Mar. 3, 2011

Related U.S. Application Data

(60) Provisional application No. 61/232,177, filed on Aug. 7, 2009.

(51) Int. Cl.
C07D 239/47 (2006.01)
A01N 43/54 (2006.01)
C07D 401/06 (2006.01)
C07D 403/06 (2006.01)
C07D 405/06 (2006.01)
C07D 409/04 (2006.01)
C07D 409/12 (2006.01)
C07D 409/14 (2006.01)

(52) U.S. Cl.
CPC ............ C07D 239/47 (2013.01); C07D 401/06 (2013.01); C07D 403/06 (2013.01); C07D 405/06 (2013.01); C07D 409/04 (2013.01); C07D 409/12 (2013.01); C07D 409/14 (2013.01)
USPC .......................................... 514/274; 544/317

(58) Field of Classification Search
CPC .............................. C07D 239/47; A01N 43/54
USPC .......................................... 544/317; 514/274
See application file for complete search history.

(56) References Cited

U.S. PATENT DOCUMENTS

| 3,309,359 A | 3/1967 | Duschinsky et al. |
| 3,368,938 A | 2/1968 | Berger et al. |
| 3,868,373 A | 2/1975 | Hoffer |
| 4,845,081 A | 7/1989 | Sloan |
| 4,996,208 A | 2/1991 | Lindner et al. |
| 5,962,489 A | 10/1999 | Mueller et al. |
| 6,066,638 A | 5/2000 | Bereznak et al. |
| 6,617,330 B2 | 9/2003 | Walter |
| 7,914,799 B2 | 3/2011 | Jira et al. |
| 2003/0039667 A1 | 2/2003 | Jira et al. |
| 2008/0004253 A1 | 1/2008 | Branstetter et al. |
| 2008/0182847 A1* | 7/2008 | Augeri et al. ................. 514/249 |
| 2008/0269238 A1 | 10/2008 | Sugihara et al. |
| 2009/0203647 A1 | 8/2009 | Benko et al. |
| 2010/0022538 A1 | 1/2010 | Boebel et al. |
| 2011/0034493 A1 | 2/2011 | Boebel et al. |

FOREIGN PATENT DOCUMENTS

| EP | 0102908 A1 | 3/1984 |
| EP | 0139613 A1 | 5/1985 |
| EP | 0332579 A2 | 9/1989 |
| EP | 0877022 B1 | 4/2003 |
| GB | 1461184 A | 1/1977 |
| JP | 6001793 A | 1/1994 |
| WO | WO9733890 A1 | 9/1997 |
| WO | WO2009/094442 A2 | 7/2009 |
| WO | WO2010047866 A2 | 4/2010 |
| WO | WO2010085377 A2 | 7/2010 |

OTHER PUBLICATIONS

International Search Report and Written Opinion for PCT/US2012/050930, Oct. 15, 2012.
International Search Report for PCT/US2010/044579, Sep. 21, 2010.
Chiacchio U, et al. Enantioselective Syntheses and Cytotoxicity of N,O-Nucleosides. Journal of Medicinal Chemistry, Jan. 1, 2003, vol. 46, pp. 3696-3702.
Morris J Robins, et al. A direct synthesis of 5-fluorocytosine and its nucleosides using trifluoromethyl hypofluorite. Journal of the Chemical Society, Chemical Communications, No. 1, Jan. 1, 1972, p. 18.
Arthur F. Lewis et al. Synthesis and in vitro anti-human cytomegalovirus (hcmv) activity of certain alkenyl substituted cytosines and 5-halocytosines. Journal of Heterocyclic Chemistry, Sep. 1, 1995, vol. 32, Nr:5, pp. 1513-1515.
Kulikowski et al. Methylation and tautomerism of 5-fluorocytosine nucleosides and their analogues. Journal Nucleic Acids Research, Jan. 1, 1978, vol. 4, pp. S7-S10.
Supplemental European Search Report for EP10807172 (PCT/US2010/044579), Dec. 7, 2012.
International Search Report for PCT/US2010/044592, Sep. 21, 2010.
International Search Report for PCT/US/2009/031683, Jan. 22, 2009.
Jaworski et al. Infrared spectra and tautomerism of 5-fluorocytosine, 5-bromocytosine and 5-iodocytosine. Matrix isolation and theoretical ab initio studies. Journal of Molecular Structure, Jan. 1, 1990, vol. 223, pp. 63-92.

(Continued)

Primary Examiner — Deepak Rao
(74) Attorney, Agent, or Firm — C. W. Arnett; Faegre Baker Daniels, LLP

(57) ABSTRACT

This present disclosure is related to the field of 5-fluoropyrimidinones and their derivatives and to the use of these compounds as fungicides.

11 Claims, No Drawings

(56) References Cited

OTHER PUBLICATIONS

Gabriella et al. Some 5-fluorosulfanilamidopyrimidines. Gazzetta Chimica Italiana, Jan. 1, 1963, vol. 93, Nr:10, pp. 1268-1278.

Zhang et al., Improved method for synthesis of 5-fluorocytosine (5-FC). CAPLUS Abstract 111:134074 (1989).

International Search Report for PCT/US2011/020351, Mar. 14, 2011.

Liang et al., A facile synthesis and herbicidal activities of novel fluorine-containing thiazolo[4,5-d] pyrimidin-7(6H)-ones. Journal of Fluorine Chemistry [online], Jul. 2007, vol. 128, Iss. 7, pp. 879-884.

Bera et al., Nucleosides with furanyl scaffolds. Tetrahedron, Jun. 10, 2002, vol. 58, Nr:24, pp. 4865-4871.

Duschinsky et al., Cytosine derivatives. CAPLUS Abstract 61:18527, 1964.

International Search Report for PCT/US2010/044588, Oct. 1, 2010.

International Search Report for PCT/US2012/050931, Oct. 9, 2012.

Waring, M J, Defining optimum lipophilicity and molecular weight ranges for drug candidates-Molecular weight dependent lower logD limits based on permeability. Bioorganic & Medical Chemistry Letters, May 15, 2009, vol. 19, Nr: 10, pp. 2844-2851.

International Search Report for PCT/US2010/060792, Apr. 22, 2011.

Duschinsky et al., Nucleosides. XXXIII. N4-Acylated 5-Fluorocytosines and a Direct Synthesis of 5-Fluoro-2'-deoxycytidine. Journal of Medicinal Chemistry, Jul. 1, 1966, vol. 9, Nr:4, pp. 566-572.

International Search Report for PCT/US2010/044576, Sep. 23, 2010.

International Searching Authority, Written Opinion for PCT/US2010/044579, 3 pages, Sep. 21, 2010.

International Searching Authority, International Preliminary Report on Patentability for PCT/US2010/044579, 4 pages, Feb. 7, 2012.

European Patent Office, Supplementary European Search Report for Application EP 10 80 7172, 6 pages, Dec. 19, 2012.

\* cited by examiner

5-FLUOROPYRIMIDINONE DERIVATIVES

CROSS REFERENCE TO RELATED APPLICATIONS

This application claims the benefit of U.S. Provisional Patent Application Ser. No. 61/232,177 filed Aug. 7, 2009.

BACKGROUND AND SUMMARY OF THE INVENTION

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to 5-fluoropyrimidinone compounds and their use as fungicides. The compounds of the present disclosure may offer protection against ascomycetes, basidiomycetes, deuteromycetes and oomycetes.

One embodiment of the present disclosure may include compounds of Formula I:

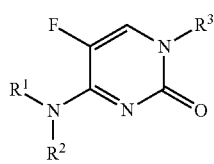

Formula I wherein $R^1$ is:
H;
$C_1$-$C_6$ alkyl optionally substituted with 1-3 $R^4$;
$C_1$-$C_6$ alkenyl optionally substituted with 1-3 $R^4$;
$C_3$-$C_6$ alkynyl optionally substituted with 1-3 $R^4$;
phenyl or benzyl wherein each of the phenyl or the benzyl may be optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$;
—$(CHR^6)_m OR^7$;
—$(CHR^6)_m N(R^9)R^{10}$;
—$C(=O)R^8$;
—$C(=S)R^8$;
—$S(O)_2 R^8$;
—$C(=O)OR^8$;
—$C(=S)OR^8$;
—$(CHR^6)_m N(R^9)R^{10}$;
—$C(=O)N(R^9)R^{10}$; or
—$C(=S)N(R^9)R^{10}$;
wherein m is an integer 1-4;
$R^2$ is:
H; or
$C_1$-$C_6$ alkyl optionally substituted with $R^4$;
alternatively $R^1$ and $R^2$ may be taken together to form:
=$CR^{11} N(R^{12})R^{13}$;
$R^3$ is:
$C_1$-$C_6$ alkyl optionally substituted with 1-3 $R^4$, $C_1$-$C_6$ haloalkyl, $C_1$-$C_6$ hydroxyalkyl, $C_2$-$C_6$ alkoxyalkyl, $C_2$-$C_6$ haloalkoxyalkyl, $C_2$-$C_6$ alkenyl optionally substituted with $R^{14}$, $C_2$-$C_6$ haloalkenyl, $C_3$-$C_6$ alkynyl, phenyl or benzyl wherein each of the phenyl or the benzyl may be optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$;
—$(CHR^6)_m OR^7$;
—$(CHR^6)_m SR^8$; or
—$(CHR^6)_m N(R^9)R^{10}$;
$R^4$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, halothio, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, $C_3$-$C_6$ trialkylsilyl, phenyl optionally substituted with 1-3 $R^5$, or with a 5- or 6-membered saturated or unsaturated ring containing 1-3 heteroatoms wherein each ring may be optionally substituted with 1-3 $R^5$;
$R^5$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, halothio, amino, $C_1$-$C_6$ alkylamino, $C_2$-$C_6$ dialkylamino, $C_2$-$C_6$ alkoxycarbonyl, $C_2$-$C_6$ alkylcarbonyl, $C_1$-$C_6$ alkylsulfonyl, nitro, hydroxyl, or cyano;
$R^6$ is H, $C_1$-$C_6$ alkyl, $C_1$-$C_6$ alkoxy, $C_1$-$C_6$ alkoxycarbonyl, phenyl or benzyl wherein each of the phenyl or the benzyl may be optionally substituted with 1-3 $R^5$;
$R^7$ is H, $C_1$-$C_8$ alkyl, $C_2$-$C_6$ alkenyl, $C_3$-$C_6$ alkynyl, $C_1$-$C_6$ haloalkyl, $C_1$-$C_6$ alkoxyalkyl, $C_2$-$C_6$ trialkylsilyl, $C_2$-$C_6$ trialkylsilylalkyl $C_2$-$C_6$ alkylcarbonyl, $C_1$-$C_6$ alkoxycarbonyl, phenyl or benzyl wherein each of the phenyl or the benzyl may be optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$;
$R^8$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl may be optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$;
$R^9$ is H, $C_1$-$C_6$ alkyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl may be optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$;
$R^{10}$ is H, $C_1$-$C_6$ alkyl, $C_1$-$C_6$ haloalkyl, $C_1$-$C_6$ alkoxyalkyl, $C_2$-$C_6$ alkylcarbonyl, or benzyl, wherein the benzyl may be optionally substituted with 1-3 $R^5$;
alternatively $R^9$ and $R^{10}$ may be taken together to form a 5- or 6-membered saturated or unsaturated ring containing 1-3 heteroatoms wherein each ring may be optionally substituted with 1-3 $R^5$;
$R^{11}$ is H or $C_1$-$C_4$ alkyl;
$R^{12}$ is H, cyano, hydroxyl, $C_1$-$C_4$ alkyl, $C_1$-$C_6$ alkoxy, $C_2$-$C_6$, alkylcarbonyl, phenyl or benzyl wherein each of the phenyl or the benzyl may be optionally substituted with 1-3 $R^5$; or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$;

alternatively $R^{11}$ and $R^{12}$ may be taken together to form a 5- or 6-membered saturated or unsaturated ring containing 1-3 heteroatoms wherein each ring may be optionally substituted with 1-3 $R^5$;

$R^{13}$ is H, $C_1$-$C_4$ alkyl, $C_1$-$C_6$ alkoxy, $C_2$-$C_6$, alkylcarbonyl, phenyl or benzyl wherein each of the phenyl or the benzyl may be optionally substituted with 1-3 $R^5$; or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$; and alternatively $R^{12}$ and $R^{13}$ may be taken together to form a 5- or 6-membered saturated or unsaturated ring containing 1-3 heteroatoms wherein each ring may be optionally substituted with 1-3 $R^5$.

$R^{14}$ is phenyl or benzyl wherein each of the phenyl or the benzyl may be optionally substituted with 1-3 $R^5$.

Another embodiment of the present disclosure may include a fungicidal composition for the control or prevention of fungal attack comprising the compounds described below and a phytologically acceptable carrier material.

Yet another embodiment of the present disclosure may include a method for the control or prevention of fungal attack on a plant, the method including the steps of applying a fungicidally effective amount of one or more of the compounds described below to at least one of the fungus, the plant, an area adjacent to the plant, and the seed adapted to produce the plant.

The term "alkyl" refers to a branched, unbranched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including ethenyl, propenyl, butenyl, isopropenyl, isobutenyl, cyclohexenyl, and the like.

The term "alkynyl" refers to a branched or unbranched carbon chain containing one or more triple bonds including propynyl, butynyl and the like.

As used throughout this specification, the term 'R' refers to the group consisting of $C_{2-8}$ alkyl, $C_{3-8}$ alkenyl or $C_{3-8}$ alkynyl, unless stated otherwise.

The term "alkoxy" refers to an —OR substituent.

The term "alkoxycarbonyl" refers to a —C(O)—OR substituent.

The term "alkylcarbonyl" refers to a —C(O)—R substituent.

The term "alkylsulfonyl" refers to an —SO$_2$—R substituent.

The term "haloalkylsulfonyl" refers to an —SO$_2$—R substituent where R is fully or partially substituted with Cl, F, I, or Br or any combination thereof.

The term "alkylthio" refers to an —S—R substituent.

The term "haloalkylthio" refers to an alkylthio, which is substituted with Cl, F, I, or Br or any combination thereof.

The term "halothio" refers to a sulfur substituted with three or five F substituents.

The term "alkylaminocarbonyl" refers to a —C(O)—N(H)—R substituent.

The term "dialkylaminocarbonyl" refers to a —C(O)—NR$_2$ substituent.

The term "alkylcycloalkylamino" refers to a cycloalkylamino substituent that is substituted with an alkyl group.

The term "trialkylsilyl" refers to —SiR$_3$.

The term "cyano" refers to a —C≡N substituent.

The term "hydroxyl" refers to an —OH substituent.

The term "amino" refers to a —NH$_2$ substituent.

The term "alkylamino" refers to a —N(H)—R substituent.

The term "dialkylamino" refers to a —NR$_2$ substituent.

The term "trialkylsilylalkyl" refers to a —SiR$_3$ substituent on an alkyl.

The term "alkoxyalkoxy" refers to —O(CH$_2$)$_n$O(CH$_2$)$_m$CH$_3$ where n is an integer from 1-3 and m is 0-2.

The term "alkoxyalkyl" refers to an alkoxy substitution on an alkyl.

The term "haloalkoxyalkyl" refers to an alkoxy substitution on an alkyl which is fully or partially substituted with Cl, F, Br, or I, or any combination thereof.

The term "hydroxyalkyl" refers to an alkyl which is substituted with a hydroxyl group.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "haloalkenyl" refers to an alkenyl, which is substituted with Cl, F, I, or Br or any combination thereof.

The term "haloalkynyl" refers to an alkynyl which is substituted with Cl, F, I, or Br or any combination thereof.

The term "halogen" or "halo" refers to one or more halogen atoms, defined as F, Cl, Br, and I.

The term "hydroxycarbonyl" refers to a —C(O)—OH substituent.

The term "nitro" refers to a —NO$_2$ substituent.

Throughout the disclosure, reference to the compounds of Formula I is read as also including optical isomers and salts of Formula I, and hydrates thereof. Specifically, when Formula I contains a branched chain alkyl group, it is understood that such compounds include optical isomers and racemates thereof. Exemplary salts include: hydrochloride, hydrobromide, hydroiodide, and the like. Additionally, the compounds of Formula I may include tautomeric forms.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

Additional features and advantages of the present invention will become apparent to those skilled in the art upon consideration of the following detailed description of the illustrative embodiments exemplifying the best mode of carrying out the invention as presently perceived.

DETAILED DESCRIPTION OF THE DISCLOSURE

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrates, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines and blends of surfactants with mineral or vegetable oils. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyirum minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mepanipyrim, mepronil, meptyl-dinocap, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothalisopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila*, *Fusarium oxysporum*, *Gliocladium* spp., *Phlebiopsis gigantea*, *Streptomyces griseoviridis*, *Trichoderma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)

phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, 5-fluorocytosine and profungicides thereof, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamide, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad and spinetoram; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dessicant insecticides such as boric acid, diatomaceous earth and silica gel; diamide insecticides such as chlorantraniliprole, cyantraniliprole and flubendiamide; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, alpha-endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, isofenphos-methyl, methamidophos and propetamphos; phosphorodiamide insecticides such as dimefox, mazidox, mipafox and schradan; oxadiazine insecticides such as indoxacarb; oxadiazoline insecticides such as metoxadiazone; phthalimide insecticides such as dialifos, phosmet and tetramethrin; pyrazole insecticides such as tebufenpyrad, tolefenpyrad; phenylpyrazole insecticides such as acetoprole, ethiprole, fipronil, pyrafluprole, pyriprole and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, meperfluthrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tetramethylfluthrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetramic acid insecticides such as spirotetramat; tetronic acid insecticides such as spiromesifen; thiourea insecticides such as diafenthiuron; urea insecticides such as flucofuron and sulcofuron; and unclassified insecticides such as closantel, copper naphthenate, crotamiton, EXD, fenazaflor, fenoxacrim, hydramethylnon, isoprothiolane, malonoben, metaflumizone, nifluridide, plifenate, pyridaben, pyridalyl, pyrifluquinazon, rafoxanide, sulfoxaflor, triarathene and triazamate, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: amide herbicides such as allidochlor, beflubutamid, benzadox, benzipram, bromobutide, cafenstrole, CDEA, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; thioamide herbicides such as chlorthiamid; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; benzothiazole herbicides such as benzazolin; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glufosinate-P, glyphosate and piperophos; phenoxy herbicides such as bromofenoxim, clomeprop, 2,4-DEB, 2,4-DEP, difenopenten, disul, erbon, etnipromid, fenteracol and trifopsime; oxadiazoline herbicides such as methazole, oxadiargyl, oxadiazon; oxazole herbicides such as fenoxasulfone; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazole herbicides such as pyroxasulfone; benzoylpyrazole herbicides such as benzofenap, pyrasulfotole, pyrazolynate, pyrazoxyfen, and topramezone; phenylpyrazole herbicides such as fluazolate, nipyraclofen, pioxaden and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, indaziflam, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, ipfencarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as benzfendizone, bromacil, butafenacil, flupropacil, isocil, lenacil, saflufenacil and terbacil; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, ortho-dichlorobenzene, dimepiperate, endothal, fluoromidine, fluridone, fluorochloridone, flurtamone, fluthiacet, indanofan, methyl isothiocyanate, OCH, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan and tritac.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, wheat leaf blotch (*Septoria tritici*, also known as *Mycosphaerella graminicola*), apple scab (*Venturia inaequalis*), and *Cercospora* leaf spots of sugar beets (*Cercospora beticola*), leaf spots of peanut (*Cercospora arachidicola* and *Cercosporidium personatum*) and other crops, and black sigatoka of bananas (*Mycosphaerella fujiensis*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m$^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

The following examples are presented to illustrate the various aspects of the compounds of the present disclosure and should not be construed as limitations to the claims.

Example 1

Preparation of 5-fluoro-1-morpholin-4-ylmethyl-4-[(morpholin-4-ylmethyl)amino]-1H-pyrimidin-2-one (1)

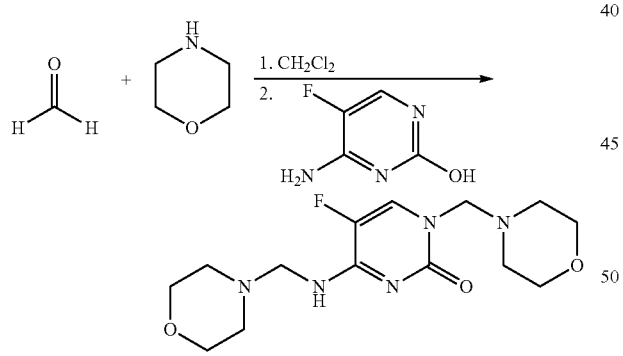

This material was prepared as described in *Int. J. Pharm.* 1987, 35, 243-252. To a mixture of paraformaldehyde (240 milligrams (mg), 8 millimoles (mmol) of monomer) in dichloromethane (CH$_2$Cl$_2$; 20 mL) in a 25 milliliter (mL) screw-cap vial was added morpholine (697 mg, 8 mmol). The reaction mixture was agitated on an orbital shaker overnight at room temperature. 4-Amino-5-fluoropyrimidin-2-ol* (250 mg, 2 mmol) was added, and the resulting heterogeneous mixture was agitated at room temperature for 48 hours (h). The reaction mixture was evaporated to dryness and the residue was treated with ether (Et$_2$O) to give a white solid, which was filtered and dried to give the title compound (381 mg, 65%): mp 156-158° C.; $^1$H NMR (300 MHz, CDCl$_3$) δ 7.46 (d, J=2.5 Hz, 1H), 5.69 (br t, 1H), 4.53 (s, 2H), 4.46 (d, J=2.6 Hz, 2H), 3.72 (m, 8H), 2.64 (m, 8H); IR (ATR) 3483 (br), 3293 (br), 1680 (s), 1639 (s), 1574 (s), 1521 (s) cm$^{-1}$.

*4-Amino-5-fluoropyrimidin-2-ol can be purchased commercially.

Example 2

Preparation of 5-fluoro-1-(4-methylpiperazin-1-ylmethyl)-4-[(4-methylpiperazin-1-ylmethyl)-amino]-1H-pyrimidin-2-one (2)

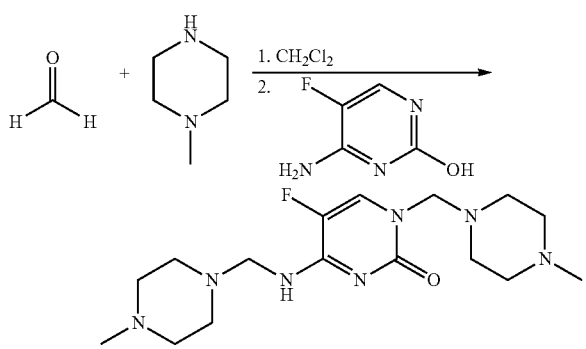

This material was prepared as described in *Int. J. Pharm.* 1987, 35, 243-252. To a mixture of paraformaldehyde (240 mg, 8 mmol of monomer) in CH$_2$Cl$_2$ (20 mL) in a 25 mL screw-cap vial was added N-methylpiperazine (813 mg, 8 mmol). The reaction mixture was agitated on an orbital shaker overnight at room temperature. 4-Amino-5-fluoropyrimidin-2-ol (250 mg, 2 mmol) was added and the resulting heterogeneous mixture was agitated at room temperature for 48 h. The reaction mixture was evaporated to dryness and the residue was treated with Et$_2$O to give a beige solid, which was filtered and dried to give the title compound (247 mg, 31%): mp 165-166° C.; $^1$H NMR (300 MHz, CDCl$_3$) δ 7.45 (d, J=2.5 Hz, 1H), 5.62 (br t, 1H), 4.55 (s, 2H), 4.5 (d, J=2.6 Hz, 2H), 2.69 (m, 8H), 2.44 (br, 8H), 2.38 (s, 6H); IR (ATR) 3465 (br), 1679 (s), 1646 (s), 1574 (s), 1522 (s) cm$^{-1}$.

Compound 3 in Table I was synthesized as in Example 2.

Example 3

Preparation of N'-[5-fluoro-1-(4-fluorobenzyl)-2-oxo-1,2-dihydro-pyrimidin-4-yl]-N,N-dimethylformamidine (4)

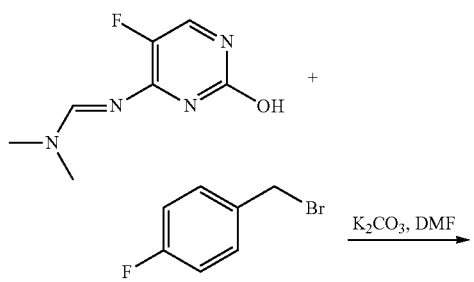

-continued

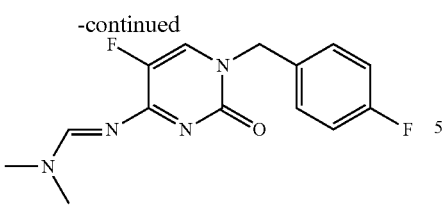

To an 8 mL screw-cap vial was added N,N-dimethylformamide (DMF; 1.5 mL), N'-(5-fluoro-2-hydroxypyrimidin-4-yl)-N,N-dimethylformamidine (100 mg, 0.54 mmol), anhydrous potassium carbonate ($K_2CO_3$; 138 mg, 1.0 mmol), and 4-fluorobenzyl bromide (113 mg, 0.60 mmol). The mixture was shaken and heated to 70° C. for 2 h and then at room temperature for an additional 16 h. The crude reaction mixture was filtered and placed directly onto a reverse phase chromatography column. After elution, the title compound was isolated as a white solid (30 mg, 20%): mp 134-136° C.; $^1H$ NMR (300 MHz, $CDCl_3$) δ 8.68 (s, 1H), 8.07 (d, J=2.5 Hz, 1H), 7.49-7.43 (m, 2H), 7.10-7.01 (m, 2H), 5.33 (s, 2H), 3.20 (s, 3H), 3.18 (s, 3H); ESIMS m/z 293 ($[M+H]^+$).

Compounds 5-7 in Table I were synthesized as in Example 3.

Example 4

Preparation of N-(5-fluoro-1-methyl-2-oxo-1,2-dihydro-pyrimidin-4-yl)-4-methyl-benzamide (8)

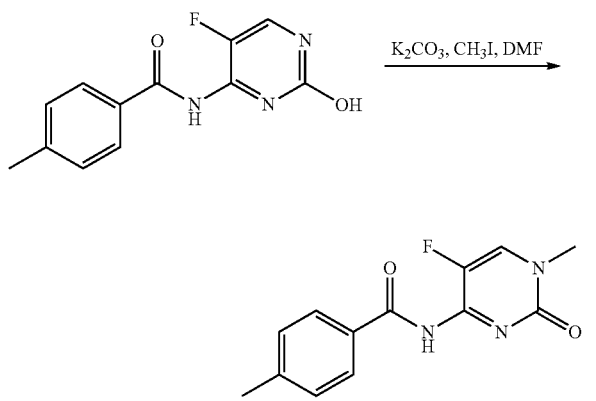

To N-(5-fluoro-2-hydroxypyrimidin-4-yl)-4-methylbenzamide (200 mg, 0.81 mmol) in DMF (5 mL) was added $K_2CO_3$ (224 mg, 1.6 mmol), and iodomethane (230 mg, 1.6 mmol). The mixture was stirred and heated to 60° C. for 30 min and then stirred for 16 h at room temperature. The mixture was partitioned between ethyl acetate (EtOAc) and water ($H_2O$). The organic phase was dried over magnesium sulfate ($MgSO_4$), filtered and evaporated. The crude material was purified by reverse phase chromatography to yield the title compound as a white solid (17 mg, 8%): mp 229-230° C.; $^1H$ NMR (300 MHz, $CDCl_3$) δ13.2 (br s, 1H), 8.23-8.15 (br m, 2H), 7.42-7.37 (br m, 1H), 7.30-7.25 (br m, 2H), 3.45 (s, 3H), 2.44 (s, 3H); ESIMS m/z 262 ($[M+H]^+$), m/z 260 ($[M-H]^-$).

Example 5

Preparation of N-(5-fluoro-1-methyl-2-oxo-1,2-dihydropyrimidin-4-yl)-N-methyl-C-phenylmethanesulfonamide (9)

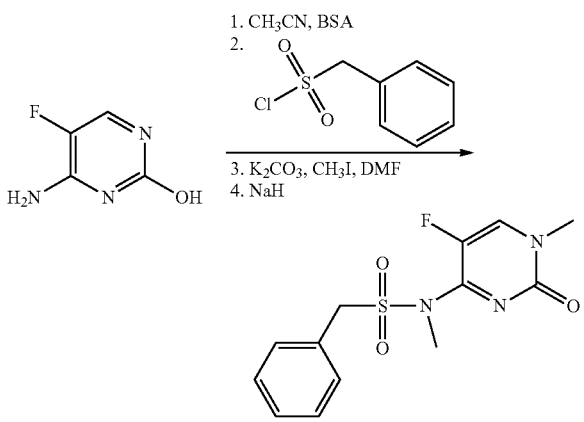

4-Amino-5-fluoropyrimidin-2-ol (2 grams (g), 15.5 mmol) was stirred in acetonitrile ($CH_3CN$; 80 mL) at 50° C. To the warm mixture was added N,O-bis(trimethylsilyl)acetamide (BSA; 9.4 g, 46.3 mmol), and stiffing and heating were continued for 1.5 h. Phenylmethanesulfonyl chloride (3.2 g, 16.8 mmol) was added. After 2 h, the reaction mixture was cooled to room temperature and partitioned between $CH_3CN$ and brine. The organic phase was dried over $MgSO_4$, filtered, evaporated and placed directly onto a silica gel column which was eluted (gradient, 0 to 100% EtOAc in petroleum ether). Combining fractions containing the major UV absorbing portion of the product mixture yielded a white solid which was used without further purification. To a portion of this material (100 mg) was added DMF (3 mL), $K_2CO_3$ (100 mg), and iodomethane (100 mg), and the mixture was stirred at 60° C. for 1 h. The reaction mixture was cooled to room temperature and an excess of sodium hydride (NaH; 60% dispersion in mineral oil) was added. The whole mixture was stirred for 30 min and then heated to 45° C. for 2.5 h. The crude mixture was filtered and purified by reverse phase chromatography followed by normal phase chromatography (gradient, 30 to 100% EtOAc in petroleum ether) to yield the title compound as a white solid (28 mg, 27%): mp 159-160° C.; $^1H$ NMR (300 MHz, $CDCl_3$) δ 7.6 (m, 1H), 7.42-7.41 (m, 2H), 7.38-7.36 (m, 3H), 4.8 (s, 2H), 3.5 (s, 3H), 2.82 (s, 3H); ESIMS m/z 312 ($[M+H]^+$), m/z 310 ($[M-H]^-$).

Example 6

Preparation of (5-fluoro-1-methyl-2-oxo-1,2-dihydropyrimidin-4-yl)carbamic acid isobutyl ester (10) and (5-fluoro-1-methyl-2-oxo-1,2-dihydropyrimidin-4-yl)methylcarbamic acid isobutyl ester (11)

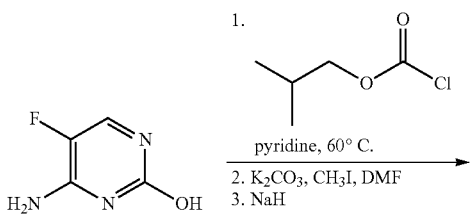

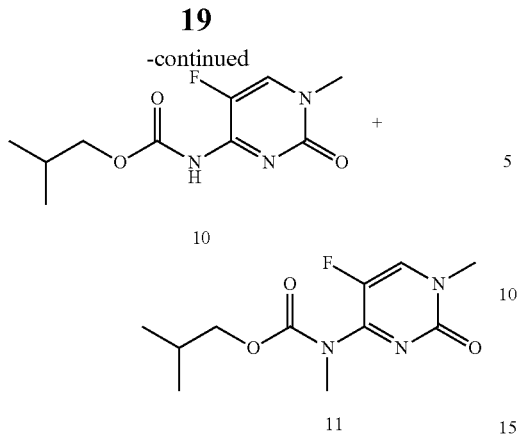

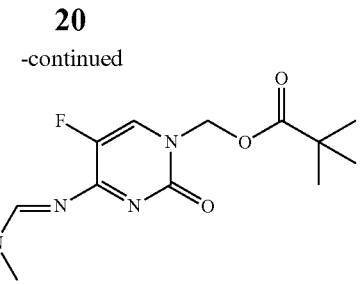

4-Amino-5-fluoropyrimidin-2-ol (0.5 g, 3.9 mmol) and isobutyl chloroformate (0.58 g, 4.2 mmol) were shaken in pyridine (5 mL) at 60° C. for 1.5 h. The crude mixture was partitioned between EtOAc and 1 N hydrochloric acid (HCl). The organic phase was dried over MgSO$_4$, filtered and evaporated. The residue was precipitated from ethyl alcohol (EtOH) to furnish a white solid which was used without further purification. A portion of this material (100 mg), K$_2$CO$_3$ (125 mg), and iodomethane (125 mg) were added to DMF (3 mL), and the mixture was stirred at 60° C. for 1 h. The mixture was cooled to room temperature and an excess of NaH (60% dispersion in mineral oil) was added. The entire mixture was stirred for 30 min and then heated to 45° C. for 2 h. The crude mixture was filtered and purified by reverse phase chromatography to yield the title compounds.

(5-Fluoro-1-methyl-2-oxo-1,2-dihydropyrimidin-4-yl)carbamic acid isobutyl ester was isolated as a white solid (16 mg): mp 126-128° C.; $^1$H NMR (300 MHz, CDCl$_3$) δ 12.2 (br s, 1H), 7.32 (br s, 1H), 3.98 (d, J=6.6 Hz, 2H), 3.4 (s, 3H), 2.02 (sept, J=6.6 Hz, 1H), 1.01 (d, J=6.6 Hz, 6H); ESIMS m/z 244 ([M+H]$^+$), m/z 242 ([M−H]$^−$). (5-Fluoro-1-methyl-2-oxo-1,2-dihydropyrimidin-4-yl)methylcarbamic acid isobutyl ester was isolated as a clear colorless oil (22 mg): $^1$H NMR (300 MHz, CDCl$_3$) δ 7.52 (d, J=5.5 Hz, 1H), 4.02 (d, J=6.8 Hz, 2H), 3.55 (s, 3H), 3.40 (s, 3H), 1.99 (sept, J=6.8 Hz, 1H), 0.95 (d, J=6.8 Hz, 6H); $^{13}$C NMR (150 MHz, CDCl$_3$) δ 158.24, 158.17, 154.7, 154.1, 140.5, 138.8, 134.0, 133.7, 73.6, 38.6, 34.9, 27.9, 19.2; ESIMS m/z 258 ([M+H]$^+$).

Example 7

Preparation of 2,2-dimethylpropionic acid 4-(dimethylamino-methyleneamino)-5-fluoro-2-oxo-2H-pyrimidin-1-ylmethyl ester (12)

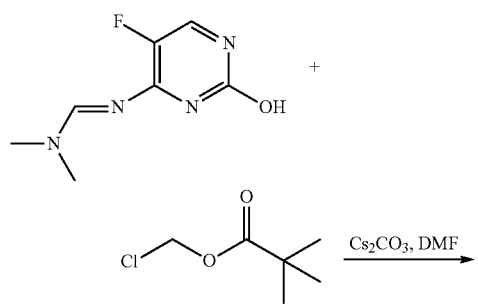

To DMF (3 mL) were added N'-(5-fluoro-2-hydroxypyrimidin-4-yl)-N,N-dimethylformamidine (100 mg, 0.54 mmol), cesium carbonate (196 mg, 0.6 mmol), and chloromethyl pivalate (90 mg, 0.6 mmol), and the mixture was shaken at room temperature for 16 h. The mixture was partitioned between EtOAc and H$_2$O. The organic phase was dried over MgSO$_4$, filtered, and evaporated. To the resultant crude oil Et$_2$O (3.5 mL) was added and a precipitate formed which was collected by filtration. The title compound was isolated as a white solid (37 mg, 23%): mp 193-194° C.; $^1$H NMR (300 MHz, DMSO-d$_6$) δ 8.67 (s, 1H), 8.07 (d, J=6.3 Hz, 1H), 5.60 (s, 2H), 3.22 (s, 3H), 3.09 (s, 3H), 1.11 (s, 9H); ESIMS m/z 299 ([M+H]$^+$).

Compound 13 in Table I was synthesized as in Example 7.

Example 8

Preparation of 4-amino-1-(benzyloxymethyl)-5-fluoropyrimidin-2(1H)-one (14) and 1-(benzyloxymethyl)-4-(benzyloxymethylamino)-5-fluoropyrimidin-2(1H)-one (15)

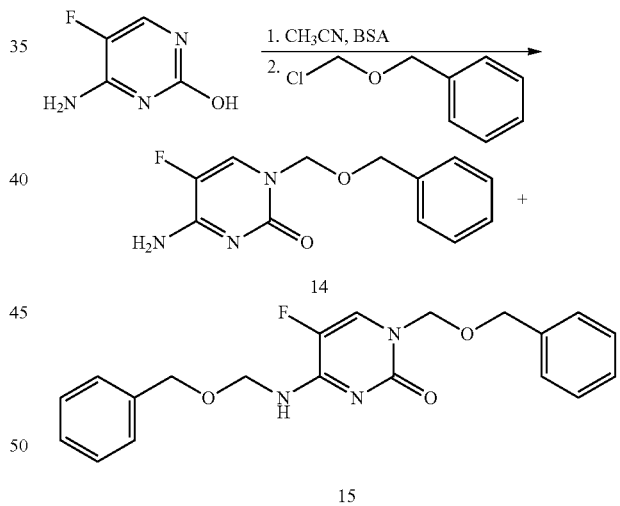

A 25 mL Schlenk-type flask was charged with 4-amino-5-fluoropyrimidin-2-ol (500 mg, 3.87 mmol), CH$_3$CN (10 mL), and BSA (1.42 mL, 5.81 mmol). The resulting white suspension was then heated at 65° C. After 90 min, the clear, colorless solution was cooled to room temperature and benzyl chloromethyl ether (1.07 mL, 7.72 mmol) was added, giving a cloudy white suspension. After stirring for 2 h at room temperature, the reaction mixture was concentrated in vacuo to give a white residue which was purified by reverse phase column chromatography yielding 4-amino-1-(benzyloxymethyl)-5-fluoropyrimidin-2(1H)-one (14; 433 mg, 45%) as a white solid: mp 213-217° C.; $^1$H NMR (400 MHz, CDCl$_3$) δ 7.98 (d, J=6.5 Hz, 1H), 7.81 (br s, 1H), 7.56 (br s, 1H), 7.24-7.36 (m, 5H), 5.11 (s, 2H), 4.54 (s, 2H); IR 3302 (s), 3082 (s), 2939 (w), 2869 (w), 1688 (s), 1619 (s), 1522 (s), 1468 (m), 1333 (m), 1131 (w), 1054 (m) cm$^{-1}$; ESIMS m/z 250 ([M+H]$^+$).

1-(Benzyloxymethyl)-4-(benzyloxymethylamino)-5-fluoropyrimidin-2(1H)-one (15; 16.5 mg, 1.2%) was obtained as a colorless oil byproduct in the synthesis of 14: $^1$H NMR (400 MHz, CDCl$_3$) δ 8.85 (t, J=5.8 Hz, 1H), 8.08 (d, J=6.6 Hz, 1H), 7.22-7.39 (m, 10H), 5.15 (s, 2H), 4.87 (d, J=5.8 Hz, 2H), 4.56 (s, 2H), 4.54 (s, 2H); IR 3248 (w), 3062 (w), 3031 (w), 1683 (s), 1644 (m), 1569 (m), 1520 (s), 1454 (w), 1357 (w), 1328 (m), 1189 (w), 1069 (m) cm$^{-1}$; ESIMS m/z 370 ([M+H]$^+$).

Compounds 16-23 in Table I were synthesized as in Example 8.

Example 9

Preparation of N'-(5-fluoro-1-methylsulfanylmethyl-2-oxo-1,2-dihydropyrimidin-4-yl)-N,N-dimethylformamidine (24)

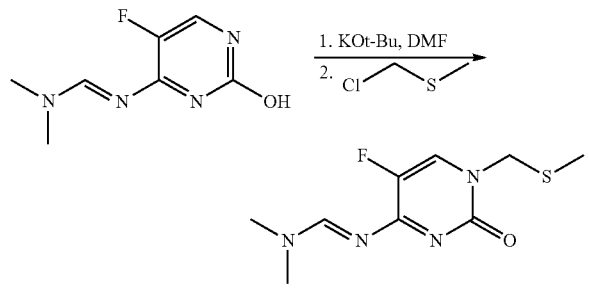

A 250 mL round bottom flask was charged with N'-(5-fluoro-2-hydroxypyrimidin-4-yl)-N,N-dimethylformamidine (1.00 g, 5.43 mmol) and DMF (55 mL) to give a white suspension. Solid potassium tert-butoxide (1.07 g, 9.53 mmol) was added, and the resulting pale yellow suspension was allowed to stir under nitrogen at room temperature for 20 min. Chloromethyl methyl sulfide (682 microliters (μL), 8.14 mmol) was then added, and the mixture was heated at 60° C. for 21 h. The crude reaction mixture was concentrated in vacuo at 55° C. to give an off-white residue which was purified by reverse phase column chromatography yielding N'-(5-fluoro-1-methylsulfanylmethyl-2-oxo-1,2-dihydropyrimidin-4-yl)-N,N-dimethylformamidine (36 mg, 25%) as a pale yellow solid: mp 132-136° C.; $^1$H NMR (400 MHz, CDCl$_3$) δ 8.68 (s, 1H), 8.20 (d, J=3.2 Hz, 1H), 5.40 (s, 2H), 3.19 (s, 3H), 3.07 (s, 3H), 2.20 (s, 3H); IR 2960 (w), 2926 (w), 1640 (s), 1582 (s), 1447 (s), 1382 (m), 1319 (m), 1269 (m), 1108 (m), 1051 (m) cm$^{-1}$; ESIMS m/z 267 ([M+Na]$^+$).

Example 10

Preparation of 4-amino-5-fluoro-1-(4-methylbenzyl)-pyrimidin-2(1H)-one (25)

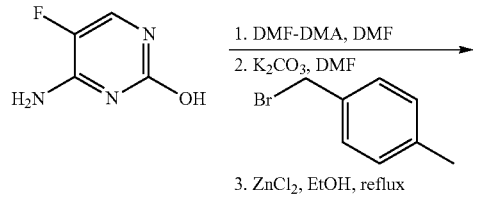

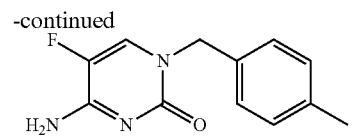

Step 1: To a magnetically stirred solution of 4-amino-5-fluoropyrimidin-2-ol (4.00 g, 31.0 mmol) in DMF (100 mL) was added N,N-dimethylformamide dimethyl acetal (DMF-DMA; 4.00 g, 34.0 mmol). The mixture was stirred at room temperature for 72 h, diluted with Et$_2$O (200 mL), and filtered. The solid product was washed with heptane to give (E)-N'-(5-fluoro-2-oxo-1,2-dihydropyrimidin-4-yl)-N,N-dimethylformimidamide (5.23 g, 92%) as a white solid: mp 240-243° C.; $^1$H NMR (300 MHz, DMSO-d$_6$) δ 10.7 (br s, 1H), 8.59 (s, 1H), 7.7 (d, J=5.6 Hz, 1H), 3.18 (s, 3H), 3.06 (s, 3H); ESIMS m/z 185 ([M+H]$^+$), m/z 183 ([M−H]$^-$).

Step 2: Powdered K$_2$CO$_3$ (325 mesh; 2.03 g, 14.7 mmol) was added to a mixture of the product from Step 1 (1.35 g, 7.35 mmol) and α-bromo-p-xylene (1.36 g, 7.35 mmol) in DMF (20 mL), under N$_2$, at room temperature. The resultant white slurry was warmed to 80° C. After stirring at 80° C. for 2 h, the reaction mixture was cooled, diluted with EtOAc (150 mL) and the solution washed with H$_2$O (4×50 mL) and saturated (satd) NaCl (1×50 mL). The organic phase was dried (Na$_2$SO$_4$), filtered and concentrated in vacuo to give 1.01 g of a light yellow solid. The crude material was dissolved in a mixture of EtOAc/CH$_2$Cl$_2$ and treated with Celite (3 g). The solvent was removed in vacuo and the residue purified by normal phase chromatography (gradient, 0 to 100% EtOAc/hexanes) to remove the isomeric O-alkylated product. The column was then eluted with 90% CH$_2$Cl$_2$/10% CH$_3$OH to obtain the desired N-alkylated product, N'-[5-fluoro-1-(4-methylbenzyl)-2-oxo-1,2-dihydropyrimidin-4-yl]-N,N-dimethylforamidine (0.668 g, 32%) as a white solid: mp 178-179° C.; $^1$H NMR (300 MHz, CDCl$_3$) δ 8.82 (s, 1H), 7.22-7.15 (m, 4H), 4.97 (s, 2H), 3.18 (s, 3H), 3.17 (s, 3H), 2.34 (s, 3H); ESIMS m/z 289 ([M+H]$^+$).

Step 3: Zinc chloride (1.24 g, 9.12 mmol) was added to a mixture of the formamidine product from Step 2 (0.656 g, 2.28 mmol) in absolute EtOH (10 mL). The resultant mixture was heated to reflux under N$_2$. The mixture gradually turned into a light yellow, homogeneous solution. After refluxing for 90 min a precipitate had formed, and after 2 h, the reaction mixture was allowed to cool to room temperature and was concentrated in vacuo. The residue was treated with CH$_2$Cl$_2$ (75 mL, slightly turbid in appearance) and washed with H$_2$O (25 mL). As soon as H$_2$O was added a white precipitate formed in both layers in the separatory funnel. The solid was removed by vacuum filtration. The solid was washed with H$_2$O followed by Et$_2$O. After air-drying overnight the white solid (0.58 g) was treated with 1:1 CH$_2$Cl$_2$/MeOH (~70 mL) and heated to reflux (turbid mixture). The mixture was filtered and the filtrate was concentrated in vacuo. The residual solid was slurried with hexanes/Et$_2$O (~3:1) and isolated by vacuum filtration, air-dried and then vacuum oven dried (70-80° C.) to give N'-(5-fluoro-2-hydroxypyrimidin-4-yl)-N,N-dimethylformamidine (0.417 g, 78%) as a white powder: mp 291-293° C. dec; $^1$H NMR (300 MHz, DMSO-d$_6$) δ 8.03 (d, J=6.9 Hz, 1H), 7.62 (br s, 1H), 7.40 (br s, 1H), 7.17 (d, J=7.8 Hz, 2H), 7.12 (d, J=8.1 Hz, 2H), 4.73 (s, 2H), 2.25 (s, 3H); $^{13}$C NMR (150 MHz, DMSO-d$_6$) δ 158.2, 154.8, 137.3, 136.3 (d, J=240 Hz), 135.3, 131.1 (d, J=30.6 Hz), 129.7, 128.3, 51.8, 21.3; ESIMS m/z 234 ([M+H]$^+$), m/z 232 ([M−H]$^-$); IR 3298

(m, br), 3100 (m, br), 1685 (s), 1619 (s), 1518 (s), 1447 (m), 1383 (m), 1343 (w), 1120 (w), 776 (w) cm⁻¹.

Example 11

Preparation of 4-amino-5-fluoro-1-(4-iodobutyl)-1H-pyrimidin-2-one (26)

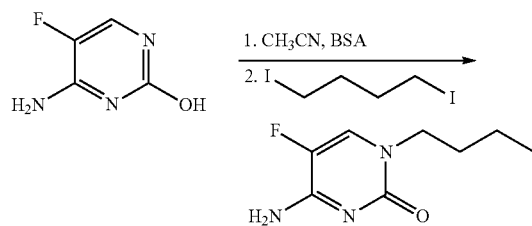

To a suspension of 4-amino-5-fluoropyrimidin-2-ol (0.50 g, 3.87 mmol) in acetonitrile (CH₃CN; 20 mL) was added BSA (1.58 g, 7.75 mmol), and the mixture was heated to 70° C. for 1 h resulting in a clear solution. After cooling to room temperature, 1,4-diiodobutane (1.2 g, 3.87 mmol) was added, and the mixture was stirred for 16 h at room temperature and then at 70° C. for 3 h. The solvent was evaporated and the residue was purified by normal phase chromatography (24 g SiO₂; gradient, 0 to 15% MeOH/CH₂Cl₂) to give an orange oil. The oil was dissolved in EtOAc and the solution was slowly cooled. The resulting solid was collected by filtration, washed with additional EtOAc, and dried to give 4-amino-5-fluoro-1-(4-iodobutyl)-1H-pyrimidin-2-one (0.52 g, 43%) as a tan solid: mp 181-184° C.; ¹H NMR (400 MHz, DMSO-d₆) δ 8.56 (s, 2H), 8.25 (d, J=6.7 Hz, 1H), 3.70 (t, J=6.7 Hz, 2H), 3.29 (t, J=6.7 Hz, 2H), 1.73 (m, 4H); ESIMS m/z 312 ([M+H]⁺).

Example 12

Preparation of 4-amino-5-fluoro-1-(4-[1,2,4]triazol-1-yl-butyl)-1H-pyrimidin-2-one (27)

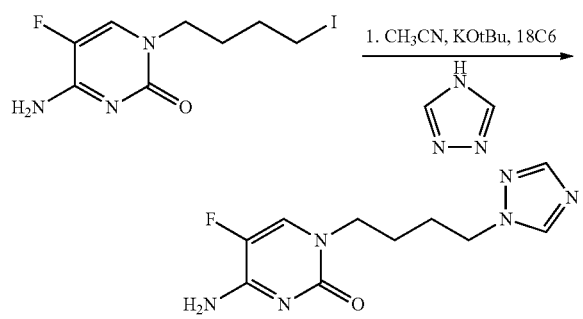

To a mixture of 1,2,4-triazole (0.044 g, 0.64 mmol), potassium ᵗbutoxide (KOᵗBu; 0.072 g, 0.64 mmol), and 18-crown-6 (18C6; 0.008 g, 0.03 mmol) in CH₃CN (3.5 mL) was added 4-amino-5-fluoro-1-(4-iodobutyl)-1H-pyrimidin-2-one (0.10 g, 0.32 mmol), and the mixture was warmed to 70° C. and stirred for 16 h. The resulting homogeneous solution was concentrated in vacuo to give the crude product as a white solid. Purification by reverse phase chromatography (13 g C18; gradient, 0 to 20% CH₃CN/water) afforded 4-amino-5-fluoro-1-(4-[1,2,4]triazol-1-yl-butyl)-1H-pyrimidin-2-one (0.023 g, 28%) as a white solid: mp 197-200° C.; ¹H NMR (400 MHz, DMSO-d₆) δ 8.50 (s, 1H), 7.94 (m, 2H), 7.56 (s, 1H), 7.35 (s, 1H), 4.19 (t, J=6.9 Hz, 2H), 3.61 (t, J=7.0 Hz, 2H), 1.73 (m, 2H), 1.51 (m, 2H); ESIMS m/z 253 ([M+H]⁺), m/z 251 ([M−H]⁻).

Example 13

Preparation of 4-amino-5-fluoro-1-methylpyrimidin-2(1H)-one (28)

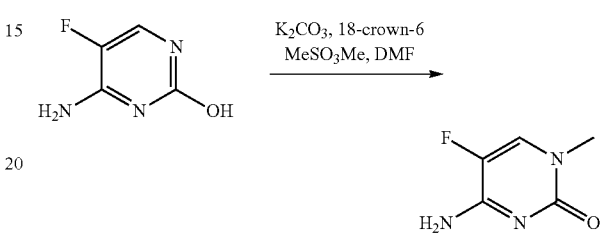

A 25 mL screw-top vial was charged with 4-amino-5-fluoropyrimidin-2-ol (151.0 mg, 1.17 mmol), K₂CO₃ (289.2 mg, 2.09 mmol), 18C6 (278.6 mg, 0.901 mmol) and anhydrous DMF (10 mL). Methyl methanesulfonate (0.0814 mL, 0.961 mmol) was added, and the resulting mixture was agitated on a rotary shaker at 85° C. for 21 h. After cooling to room temperature, the crude material was concentrated in vacuo and purified by reverse phase column chromatography to afford 4-amino-5-fluoro-1-methylpyrimidin-2(1H)-one (61.9 mg, 37%) as a beige solid: mp 195° C. (dec.); ¹H NMR (400 MHz, DMSO-d₆) δ 7.94 (d, J=6.8 Hz, 1H), 7.52 (s, 1H), 7.32 (s, 1H), 3.18 (s, 3H); ESIMS m/z 144 ([M+H]⁺.

Compounds 29-33 were prepared as in Example 13.

Example 14

Preparation of (E)-N'-(1-ethyl-5-fluoro-2-oxo-1,2-dihydropyrimidin-4-yl)-N,N-dimethylformimidamide (34)

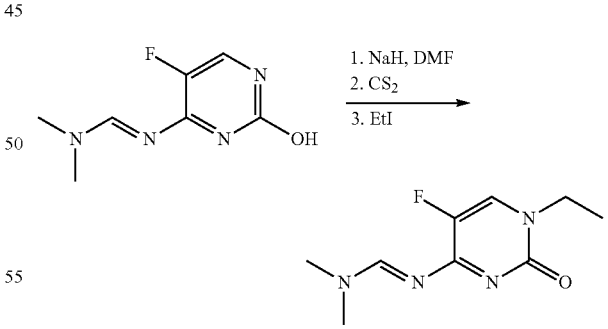

A 25 mL screw-top vial was charged with (E)-N'-(5-fluoro-2-hydroxypyrimidin-4-yl)-N,N-dimethylformimidamide (99.5 mg, 0.540 mmol), DMF (2 mL), and NaH (60% dispersion in mineral oil; 24.5 mg, 0.613 mmol) and was agitated on a rotary shaker at 50° C. for 40 min. After cooling to room temperature, carbon disulfide (0.036 mL, 0.599 mmol) was added, and the reaction mixture was agitated on a rotary shaker at room temperature for 90 min. At this point, iodoethane (0.052 mL, 0.650 mmol) was added, and the reaction mixture was further agitated at room temperature for 3.5 h, whereupon the crude mixture was concentrated in vacuo. The crude material was purified by normal phase chromatography (gradient, 0 to 30% MeOH/CH$_2$Cl$_2$) to afford (E)-N'-(1-ethyl-5-fluoro-2-oxo-1,2-dihydropyrimidin-4-yl)-N,N-dimethylformimidamide (105 mg, 67%) as a white solid: mp 157-160° C.; $^1$H NMR (400 MHz, DMSO-d$_6$) δ 8.62 (s, 1H), 8.09 (d, J=6.2 Hz, 1H), 3.70 (q, J=7.1 Hz, 2H), 3.20 (s, 3H), 3.07 (s, 3H), 1.18 (t, J=7.1 Hz, 3H); ESIMS m/z 213 ([M+H]$^+$.

Compounds 35 and 36 were prepared as in Example 14.

Example 15

Preparation of 1-(ethoxymethyl)-5-fluoro-4-(2-fluorobenzylamino)-pyrimidin-2(1H)-one (37)

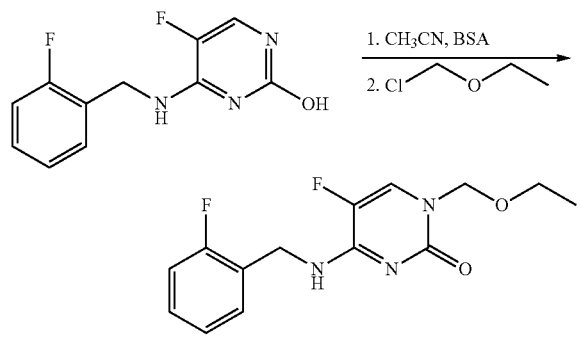

A 25 mL screw-top vial was charged with 5-fluoro-4-(2-fluorobenzylamino)pyrimidin-2-ol (49.7 mg, 0.210 mmol), CH$_3$CN (1 mL), and BSA (0.054 mL, 0.0221 mmol), and the mixture was agitated on an rotary shaker at 65° C. for 30 min. After cooling to room temperature, (chloromethoxy)ethane (0.022 mL, 0.237 mmol) was added, and the resulting mixture was agitated on a rotary shaker at room temperature for 16 h. The crude reaction mixture was concentrated in vacuo and was purified by normal phase chromatography (gradient, 0 to 25% MeOH/CH$_2$Cl$_2$) to afford 1-(ethoxymethyl)-5-fluoro-4-(2-fluorobenzylamino)-pyrimidin-2(1H)-one (55.0 mg, 89%) as a yellow oil: $^1$H NMR (400 MHz, DMSO-d$_6$) δ 8.60 (t, J=5.8 Hz, 1H), 8.05-7.95 (m, 1H), 7.40-7.26 (m, 2H), 7.26-7.10 (m, 2H), 5.01 (s, 2H), 4.59 (d, J=5.9 Hz, 2H), 3.49 (q, J=7.0 Hz, 2H), 1.09 (dd, J=9.0, 5.0 Hz, 3H); ESIMS m/z 296 ([M+H]$^+$), m/z 294 ([M–H]$^-$).

Example 16

Preparation of 5-fluoro-4-((2-fluorobenzyl)(methyl)amino)-1-(4-methylbenzyl)pyrimidin-2(1H)-one (38)

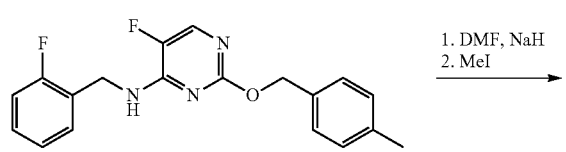

A 25 mL screw-top vial was charged with NaH (60% dispersion in mineral oil; 20.5 mg, 0.513 mmol) and DMF (2.5 mL). 5-Fluoro-N-(2-fluorobenzyl)-2-(4-methylbenzyloxy)pyrimidin-4-amine (149 mg, 0.436 mmol) was added, and the mixture was allowed to stir at room temperature. After 10 min, iodomethane (0.033 mL, 0.530 mmol) was added, and the resulting mixture was allowed to stir at room temperature for an additional 28 h. After this time, the crude reaction mixture was concentrated in vacuo and purified by normal phase chromatography (gradient, 0 to 40% EtOAc/Hexanes) to afford 5-fluoro-4-((2-fluorobenzyl)(methyl)amino)-1-(4-methylbenzyl)pyrimidin-2(1H)-one (119.7 mg, 77%) as a colorless oil: $^1$H NMR (400 MHz, DMSO-d$_6$) δ 8.16 (d, J=9.5 Hz, 1H), 7.45-7.06 (m, 8H), 4.83 (s, 2H), 4.79 (s, 2H), 3.13 (d, J=3.3 Hz, 3H), 2.27 (s, 3H); $^{13}$C NMR (101 MHz, DMSO-d$_6$) δ 160.1 (d, J=244.4 Hz), 154.9 (d, J=7.1 Hz), 152.9, 136.8, 136.2 (d, J=243.2 Hz), 134.2, 132.8 (d, J=37.3 Hz), 129.2 (d, J=8.2 Hz), 129.0, 128.7, 127.8, 124.6 (d, J=3.4 Hz), 124.0 (d, J=14.5 Hz), 115.3 (d, J=21.0 Hz), 51.0, 47.7, 37.2 (d, J=8.3 Hz), 20.6; ESIMS m/z 356 ([M+H]$^+$).

Example 17

Preparation of 4-amino-5-fluoro-1-(thiophen-3-yl)pyrimidin-2(1H)-one (39)

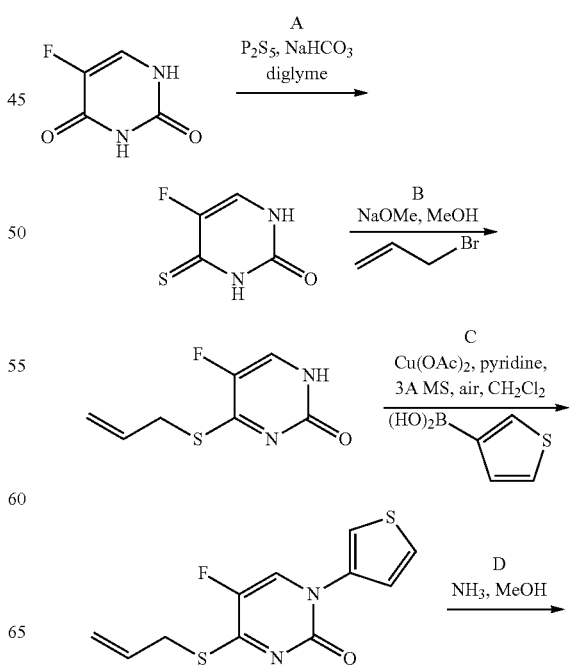

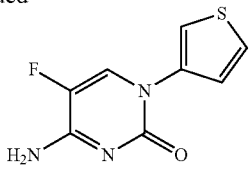

A) To a solution of phosphorus pentasulfide (102.6 g, 0.46 mol) in diglyme (1 L) was added 5-fluoropyrimidine-2,4(1H,3H)-dione (30 g, 0.23 mol). Solid sodium hydrogen carbonate ($NaHCO_3$; 77.3 g, 1.04 mol) was added at a rate determined by the evolution of carbon dioxide. The reaction mixture was stirred overnight at 110° C. The yellow mixture was cooled and poured into 1 L of cold water. The precipitated solid product was isolated by filtration and purified by normal phase chromatography (gradient, 10 to 50% EtOAc/Petroleum ether) to give 5-fluoro-4-thioxo-3,4-dihydropyrimidin-2(1H)-one (13.4 g, 40%) as a yellow solid: mp 254-255° C.; $^1$H NMR (301 MHz, DMSO-$d_6$) δ 7.81 (d, J=4.0 Hz, 1H); ESIMS m/z 145 ([M−H]$^-$).

B) This material was prepared by the procedure described in *Tetrahedron* 1985, 41, 5289-5293. To a solution of 5-fluoro-4-thioxo-3,4-dihydropyrimidin-2(1H)-one (12.4 g, 84.9 mmol) and sodium methoxide (4.54 g, 84.9 mmol) in MeOH (100 mL) was added dropwise allyl bromide (10.27 g, 84.9 mmol) at room temperature. The reaction mixture was stirred overnight at room temperature. After removal of solvent, the residue was purified by normal phase chromatography (gradient, 10 to 33% EtOAc/hexane), to give 4-(allylthio)-5-fluoropyrimidin-2(1H)-one (6 g, 38%) as a white solid: mp 150-152° C.; $^1$H NMR (301 MHz, DMSO-$d_6$) δ 11.60 (s, 1H), 8.00 (d, J=4.5 Hz, 1H), 5.90 (ddt, J=16.8, 10.0, 6.8 Hz, 1H), 5.34 (dd, J=16.9, 1.4 Hz, 1H), 5.15 (dd, J=10.0, 0.7 Hz, 1H), 3.83 (d, J=6.8 Hz, 2H); ESIMS m/z 187 ([M+H]$^+$).

C) This material was prepared by the procedure described in *J. Org. Chem.* 2006, 71, 9183-9190. To a stirred suspension of dry Cu(OAc)$_2$ (1.02 g, 5.64 mmol), 4-(allylthio)-5-fluoropyrimidin-2(1H)-one (700 mg, 3.76 mmol), thiophen-3-ylboronic acid (962 mg, 7.52 mmol), and activated 3 Å molecular sieves (2 g) in dry $CH_2Cl_2$ (30 mL) was added pyridine (595 mg, 7.52 mmol) at room temperature. The mixture was stirred for 24 h at ambient temperature in the presence of air. The reaction mixture was diluted with $CH_2Cl_2$ (30 mL), filtered through a pad of Celite, and washed with water (50 mL) in the presence of ethylenediaminetetraacetic acid (EDTA; 700 mg, 2.4 mmol). The colorless organic phase was dried over $MgSO_4$ and was concentrated in vacuo. The residue was purified by normal phase chromatography (isocratic, 2:1 petroleum ether:EtOAc) to afford 4-(allylthio)-5-fluoro-1-(thiophen-3-yl)pyrimidin-2(1H)-one (290 mg, 29%) as a yellow solid: mp 125-127° C.; $^1$H NMR (301 MHz, DMSO-$d_6$) δ 8.52-8.35 (m, 1H), 7.81 (s, 1H), 7.69-7.55 (m, 1H), 7.32 (d, J=3.5 Hz, 1H), 6.05-5.81 (m, 1H), 5.36 (d, J=16.9 Hz, 1H), 5.18 (d, J=9.8 Hz, 1H), 3.89 (d, J=6.4 Hz, 2H); ESIMS m/z 269 ([M+H]$^+$).

D) This material was prepared by the procedure described in *J. Org. Chem.* 2006, 71, 9183-9190. 4-(Allylthio)-5-fluoro-1-(thiophen-3-yl)pyrimidin-2(1H)-one (330 mg, 1.23 mmol) was dissolved in a methanol solution of ammonia (7 N, 5 mL). The reaction mixture was stirred overnight at 100° C. in a pressure vessel. After removal of solvent, the residue was purified by preparative thin layer chromatography to give 4-amino-5-fluoro-1-(thiophen-3-yl)pyrimidin-2(1H)-one (177 mg, 68%) as a yellow solid: mp 228-229° C.; $^1$H NMR (300 MHz, DMSO-$d_6$) δ 8.11 (d, J=6.9 Hz, 1H), 7.89 (s, 1H), 7.65 (d, J=1.9 Hz, 2H), 7.56 (dd, J=5.1, 3.3 Hz, 1H), 7.29 (dd, J=5.1, 1.0 Hz, 1H); ESIMS m/z 212 ([M+H]$^+$).

Compounds 40-55 were prepared as described in Example 17.

Example 18

Preparation of (E)-N'-(5-fluoro-2-oxo-1-(thiophen-3-yl)-1,2-dihydropyrimidin-4-yl)-N,N-dimethylformimidamide (56)

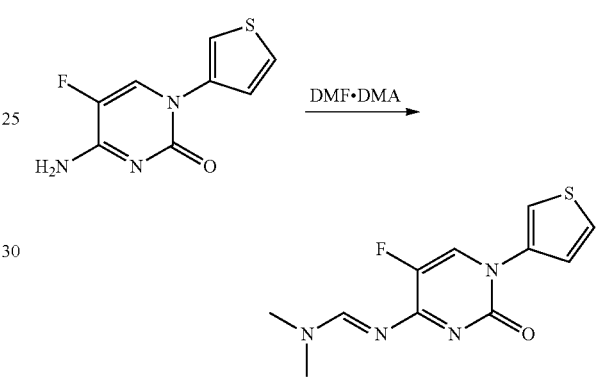

4-Amino-5-fluoro-1-(thiophen-3-yl)pyrimidin-2(1H)-one (140 mg, 0.66 mmol) was dissolved in DMF-DMA (5 mL). The reaction mixture was stirred at reflux overnight. The residual DMF-DMA was removed in vacuo, and the residue was purified by preparative thin layer chromatography to give (E)-N'-(5-fluoro-2-oxo-1-(thiophen-3-yl)-1,2-dihydropyrimidin-4-yl)-N,N-dimethylformimidamide (75 mg, 43%) as a yellow solid: mp 211-213° C.; $^1$H NMR (300 MHz, DMSO-$d_6$) δ 8.73 (s, 1H), 8.22 (d, J=6.4 Hz, 1H), 7.75 (dd, J=3.2, 1.4 Hz, 1H), 7.60 (dd, J=5.2, 3.2 Hz, 1H), 7.34 (dd, J=5.2, 1.4 Hz, 1H), 3.26 (s, 3H), 3.13 (s, 2H); ESIMS m/z 267 ([M+H]$^+$).

Compounds 57-64 were prepared as described in Example 18.

Example 19

Preparation of 5-fluoro-4-(2-fluorobenzylamino)-1-(thiophen-3-yl)pyrimidin-2(1H)-one (65)

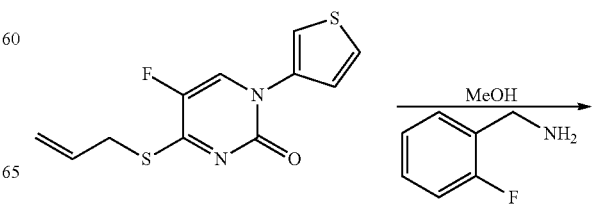

29

-continued

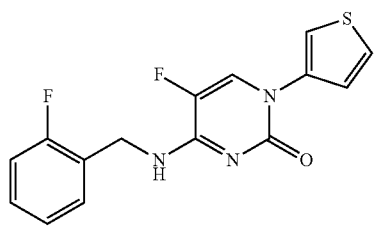

To a solution of 4-(allylthio)-5-fluoro-1-(thiophen-3-yl)pyrimidin-2(1H)-one (140 mg, 0.66 mmol) in MeOH (1 mL) was added (2-fluorophenyl)methanamine (50 mg, 0.186 mmol). The reaction mixture was heated at 100° C. for 30 min in a microwave. After cooling, the mixture was purified by preparative thin layer chromatography to give 5-fluoro-4-(2-fluorobenzylamino)-1-(thiophen-3-yl)pyrimidin-2(1H)-one (41 mg, 20%) as a white solid: mp 75-78° C.; $^1$H NMR (300 MHz, DMSO-$d_6$) δ 8.70 (s, 1H), 8.16 (d, J=7.0 Hz, 1H), 7.66 (dd, J=3.2, 1.4 Hz, 1H), 7.57 (dd, J=5.2, 3.2 Hz, 1H), 7.43-7.13 (m, 5H), 4.63 (d, J=5.5 Hz, 2H); ESIMS m/z 320 ([M+H]$^+$).

Compounds 66-73 were prepared as described in Example 19.

Example 20

Preparation of 4-amino-1-(cyclopropylmethyl)-5-fluoropyrimidin-2(1H)-one (74)

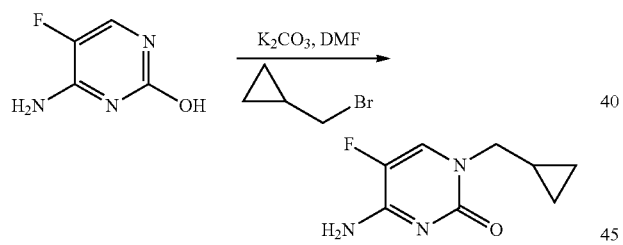

To a solution of (bromomethyl)cyclopropane (1.0 g, 7.4 mmol) in DMF (20 mL) was added molecular sieves (—2 g), and the resulting mixture was stirred at room temperature. After 1 h, 4-amino-5-fluoropyrimidin-2-ol (1.9 g, 14.8 mmol) and K$_2$CO$_3$ (5.1 g, 37 mmol) were added, and the reaction mixture was heated at 90° C. for 12 h. After cooling to room temperature, the crude reaction mixture was filtered through a Büchner funnel, and the solid residue was washed with EtOAc. The collected filtrate was concentrated in vacuo to give a residue which was purified by normal phase chromatography (isocratic, 5% MeOH/EtOAc). Following recrystallization from methyl tert-butylether, 4-amino-1-(cyclopropylmethyl)-5-fluoropyrimidin-2(1H)-one (1.12 g, 83%) was isolated as a white solid: mp 224-226° C.; $^1$H NMR (400 MHz, methanol-$d_4$) δ 7.86 (d, J=6.2 Hz, 1H), 3.61 (d, J=7.2 Hz, 2H), 1.24 (ddd, J=12.8, 7.6, 4.8 Hz, 1H), 0.65-0.50 (m, 2H), 0.39 (q, J=4.8 Hz, 2H); ESIMS m/z 184 ([M+H]$^+$).

Compounds 75-79 were prepared as described in Example 20.

30

Example 21

Preparation of ethyl 1-(cyclopropylmethyl)-5-fluoro-2-oxo-1,2-dihydropyrimidin-4-ylcarbamate (80)

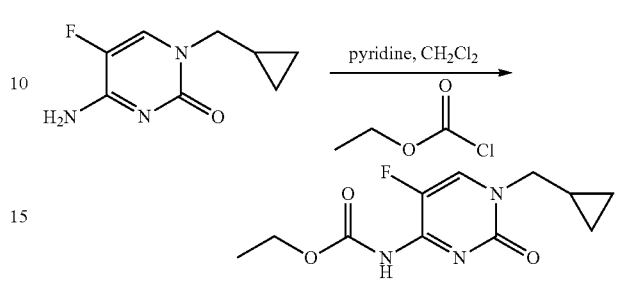

4-Amino-1-(cyclopropylmethyl)-5-fluoropyrimidin-2(1H)-one (200 mg, 1.09 mmol) was dissolved in CH$_2$Cl$_2$ (0.90 mL) and pyridine (172.4 mg, 2.18 mmol) at room temperature and then was cooled to −20° C. Ethyl chloroformate (166 mg, 1.53 mmol) was then added to the reaction mixture dropwise, keeping the reaction temperature between −20 and −5° C. After the addition was complete, the reaction was allowed to warm slowly to room temperature and stirred for 2 h. The reaction mixture was filtered, and the solids were rinsed with EtOAc (15 mL×3). The filtrate was concentrated in vacuo, and purified by preparative thin layer chromatography, to afford ethyl 1-(cyclopropylmethyl)-5-fluoro-2-oxo-1,2-dihydropyrimidin-4-ylcarbamate (70 mg, 30%) as a pale yellow solid: mp 90-92° C.; $^1$H NMR (400 MHz, methanol-$d_4$) δ 8.20 (s, 1H), 4.26 (q, J=7.1 Hz, 2H), 3.70 (d, J=7.2 Hz, 2H), 1.24-1.36 (m, 4H), 0.65-0.57 (m, 2H), 0.46-0.39 (m, 2H); ESIMS m/z 256 ([M+H]$^+$).

Compounds 81-84 were prepared as described in Example 21.

Example 22

Preparation of 1-(2-chlorophenyl)-3-(1-(cyclopropylmethyl)-5-fluoro-2-oxo-1,2-dihydropyrimidin-4-yl)urea (85)

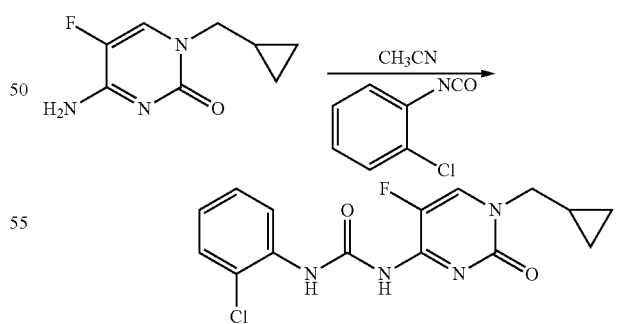

To a stirred solution of 4-amino-1-(cyclopropylmethyl)-5-fluoropyrimidin-2(1H)-one (150 mg, 0.819 mmol) in dry CH$_3$CN (7.5 mL) at room temperature and under nitrogen was added 2-chlorophenylisocyanate (138.3 mg, 0.90 mmol). After stirring for 1 h, the crude reaction mixture was filtered, and the solids were rinsed with CH$_3$CN (10 mL). The collected filtrate was then concentrated in vacuo and dried under high vacuum to afford 1-(2-chlorophenyl)-3-(1-(cyclopropylmethyl)-5-fluoro-2-oxo-1,2-dihydropyrimidin-4-yl)urea (160 mg, 58%) as an off-white solid: mp 197-199° C.; $^1$H NMR (400 MHz, methanol-d$_4$) δ 8.26 (d, J=6.0 Hz, 1H), 8.21 (dd, J=8.3, 1.5 Hz, 1H), 7.47 (dd, J=8.0, 1.4 Hz, 1H), 7.35-7.28 (m, 1H), 7.13 (td, J=7.8, 1.5 Hz, 1H), 3.74 (d, J=7.3 Hz, 2H), 1.32 (m, 1H), 0.69-0.58 (m, 2H), 0.50-0.38 (m, 2H); ESIMS m/z 337 ([M+H]$^+$).

Compounds 86-93 were prepared as described in Example 22.

Example 23

Preparation of N-(5-fluoro-2-oxo-1-((tetrahydrofuran-2-yl)methyl)-1,2-dihydropyrimidin-4-yl)thiophene-2-carboxamide (94)

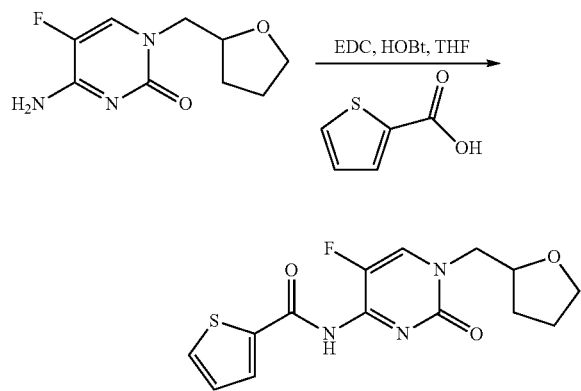

This material was prepared by the procedure described in *J. Org. Chem.* 2005, 70, 7459-7467. To a solution of 4-amino-5-fluoro-1-((tetrahydrofuran-2-yl)methyl)pyrimidin-2(1H)-one (200 mg, 0.94 mmol) in dry THF (1 mL) at room temperature were added 1-ethyl-3-(3-dimethylaminopropyl)carbodiimide (EDC; 180 mg, 0.94 mmol) and 1H-benzo[d][1,2,3]triazol-1-ol (HOBt; 139 mg, 1.03 mmol). After stirring for 10 min, thiophene-2-carboxylic acid (145 mg, 1.13 mmol) was added, and the resulting solution was allowed to stir at room temperature for 12 h. The reaction mixture was concentrated in vacuo, quenched with satd aq NaHCO$_3$ solution (10 mL), and extracted with EtOAc (25 mL×3). The combined extracts were washed with satd aq sodium chloride (NaCl) solution, dried over Na$_2$SO$_4$, filtered, and concentrated by rotary evaporation. Purification by normal phase chromatography (gradient, 0 to 2% MeOH/CH$_2$Cl$_2$) afforded 4-amino-5-fluoro-1-((tetrahydrofuran-2-yl)methyl)pyrimidin-2(1H)-one (60 mg, 20%) as a white solid: mp 168-170° C.; $^1$H NMR (400 MHz, CDCl$_3$) δ 12.96 (s, 1H), 7.96 (d, J=3.7 Hz, 1H), 7.63 (d, J=5.7 Hz, 1H), 7.60 (d, J=4.9 Hz, 1H), 7.16-7.11 (m, 1H), 4.20-4.08 (m, 2H), 3.89 (dd, J=15.1, 6.9 Hz, 1H), 3.80 (dd, J=14.5, 7.5 Hz, 1H), 3.57 (dd, J=14.4, 7.7 Hz, 1H), 2.10 (dt, J=12.8, 6.7 Hz, 1H), 1.99-1.87 (m, 2H), 0.88 (m, 1H); ESIMS ink 324 ([M+H]$^+$).

Compounds 95-101 were prepared as described in Example 23.

Example 24

Preparation of 5-fluoro-1-((tetrahydrofuran-2-yl)methyl)-4-(thiophen-2-ylmethylamino)pyrimidin-2(1H)-one (102)

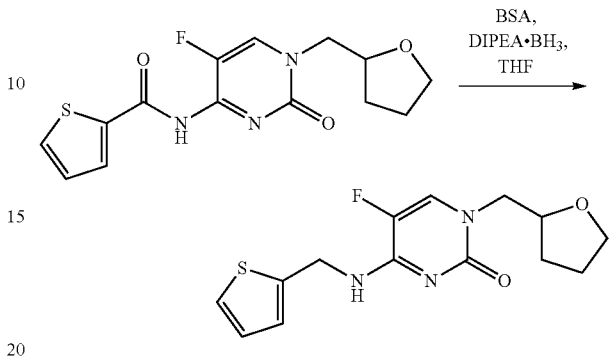

This material was prepared by the procedure described in *J. Org. Chem.* 2005, 70, 7459-7467. To a solution of 4-amino-5-fluoro-1-((tetrahydrofuran-2-yl)methyl)pyrimidin-2(1H)-one (160 mg, 0.495 mmol) in THF (4 mL) at room temperature was added BSA (0.61 mL, 2.47 mmol) dropwise. After the addition was complete, borane-N,N-diisopropylethylamine complex (DIPEA.BH$_3$; 0.90 mL, 4.95 mL) was added dropwise, and the resulting solution was stirred at room temperature for 15 min. The reaction mixture was quenched by the addition of MeOH (20 mL), and the mixture was concentrated in vacuo. The resulting mixture was dissolved in a 1:1 (v:v) mixture of 17% ammonia in methanol:28% ammonia in water (135 mL) and heated at 50° C. for 13 h. After cooling to room temperature, the mixture was extracted with chloroform (CHCl$_3$; 100 mL×2). The combined extracts were washed with aq NaCl solution, dried over Na$_2$SO$_4$, filtered, and concentrated in vacuo. Purification by preparative thin layer chromatography afforded 5-fluoro-1-((tetrahydrofuran-2-yl)methyl)-4-(thiophen-2-ylmethylamino)pyrimidin-2(1H)-one (40 mg, 26%) as a gummy white solid: $^1$H NMR (400 MHz, acetone-d$_6$) δ 7.69 (d, J=6.7 Hz, 1H), 7.52 (s, 1H), 7.32 (dd, J=5.1, 1.2 Hz, 1H), 7.08 (dd, J=3.4, 0.9 Hz, 1H), 6.95 (dd, J=5.1, 3.5 Hz, 1H), 4.85 (d, J=6.0 Hz, 2H), 4.12 (ddd, J=14.6, 7.1, 3.2 Hz, 1H), 4.00 (dd, J=13.6, 2.8 Hz, 1H), 3.83 (dt, J=8.1, 6.7 Hz, 1H), 3.72-3.64 (m, 1H), 3.56 (dd, J=13.6, 7.7 Hz, 1H), 2.02-1.93 (m, 1H), 1.86 (ddd, J=11.0, 8.1, 1.6 Hz, 2H), 1.67-1.54 (m, 1H); IR (thin film) 3222, 3125, 3068, 2950, 2875, 1673, 1623, 1586, 1556, 1508, 1368, 1329, 1186, 1139, 1065, 906 cm$^{-1}$; ESIMS ink 310 ([M+H]$^+$).

Compounds 103 and 104 were prepared as described in Example 24.

Example 25

Preparation of 5-fluoro-4-(2-fluorobenzylamino)-1-isobutyl-pyrimidin-2(1H)-one (105)

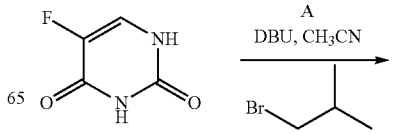

-continued

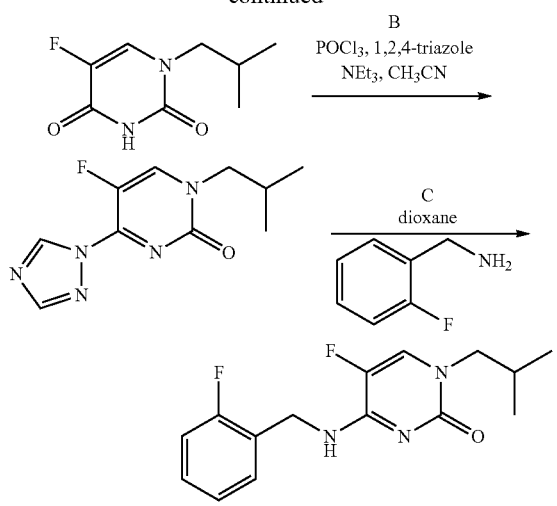

A) To a solution of 5-fluoropyrimidine-2,4(1H,3H)-dione (5.0 g, 38 mmol) and 1,8-diazabicyclo[5.4.0]undec-7-ene (DBU; 6.4 g, 42 mmol) in dry CH$_3$CN (150 mL) at room temperature and under nitrogen was added 1-bromo-2-methylpropane (5.3 g, 38 mmol) dropwise. The reaction was then heated to reflux for 18 h. After cooling to room temperature, the solvent was removed in vacuo. The crude residue was purified by normal phase chromatography (gradient, 0 to 20% EtOAc/Petroleum ether), providing 5-fluoro-1-isobutylpyrimidine-2,4(1H,3H)-dione (2.5 g, 35%) as a white solid: mp 173-174° C.; $^1$H NMR (400 MHz, CDCl$_3$) δ 8.61 (s, 1H), 7.21 (d, J=5.5 Hz, 1H), 3.53 (d, J=7.5 Hz, 2H), 2.13-2.01 (m, 1H), 0.98 (d, J=6.7 Hz, 6H); ESIMS m/z 185 ([M−H]$^-$).

B) Phosphoryl trichloride (3.3 g, 21 mmol) was added to a solution of 1,2,4-triazole (6.7 g, 97 mmol) in CH$_3$CN (53 mL) under nitrogen at room temperature. The mixture was cooled to 0° C., whereupon triethylamine (Et$_3$N, 9.5 g, 92 mmol) was added dropwise followed by the addition of a solution of 5-fluoro-1-isobutylpyrimidine-2,4(1H,3H)-dione (2.0 g, 11 mmol) in CH$_3$CN (30 mL). After stirring for 1 h at room temperature, Et$_3$N (3.6 g, 36 mmol) and then water (5 mL, 280 mmol) were added, and the reaction mixture was stirred for an additional 10 min. The crude reaction mixture was then concentrated in vacuo. Recrystallization from EtOAc/petroleum ether provided 5-fluoro-1-isobutyl-4-(1H-1,2,4-triazol-1-yl)pyrimidin-2(1H)-one (1.9 g, 74%) as an off white crystalline solid: mp 150-153° C.; $^1$H NMR (400 MHz, CDCl$_3$) δ 9.26 (s, 1H), 8.23 (s, 1H), 7.84 (d, J=5.7 Hz, 1H), 3.79 (d, J=7.4 Hz, 2H), 2.28 (dt, J=13.7, 6.9 Hz, 1H), 1.02 (d, J=6.7 Hz, 6H); ESIMS m/z 238 ([M+H]$^+$).

C) A solution of 5-fluoro-1-isobutyl-4-(1H-1,2,4-triazol-1-yl)pyrimidin-2(1H)-one (500 mg, 2.1 mmol) and 2-fluorobenzylamine (313 mg, 2.5 mmol) in dry 1,4-dioxane (10 mL) was heated to reflux for 1 h under nitrogen. After cooling to room temperature, the reaction mixture was concentrated in vacuo. Recrystallization from EtOAc/methyl tert-butylether afforded 5-fluoro-4-(2-fluorobenzylamino)-1-isobutylpyrimidin-2(1H)-one (545 mg, 89%) as an off white solid: mp 118-119° C.; $^1$H NMR (400 MHz, CDCl$_3$) δ 7.45 (td, J=7.6, 1.7 Hz, 1H), 7.35-7.28 (m, 2H), 7.13 (ddd, J=21.9, 13.9, 7.3 Hz, 3H), 5.58 (s, 1H), 4.81 (d, J=5.4 Hz, 2H), 3.56 (d, J=7.5 Hz, 2H), 2.16 (dt, J=13.6, 6.8 Hz, 1H), 0.95 (d, J=6.7 Hz, 6H); ESIMS m/z 295 ([M+H]$^+$).

Compounds 106-110 were prepared as described for Example 25.

TABLE I

Compounds and Related Characterization Data

| Cmpd | Structure | Appearance | mp (° C.) | MS | $^1$H NMR$^a$ (δ, solvent) |
|---|---|---|---|---|---|
| 3 | 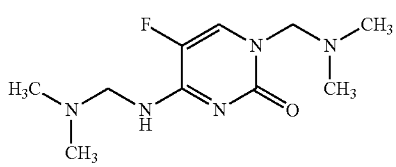 | white solid | 157-187 dec | | (CDCl$_3$) 7.47 (d, J = 6.1 Hz, 1H), 5.91 (s, 1H), 4.45 (s, 2H), 4.38 (d, J = 5.2 Hz, 2H), 2.36 (s, 12H) |
| 5 | 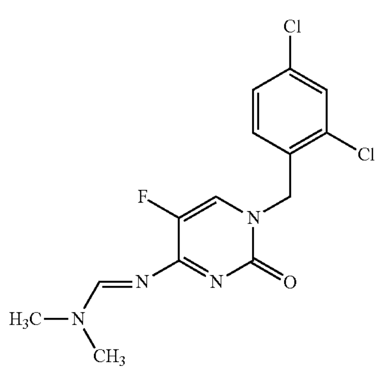 [SMILES: CN(C)/C=N/c1nc(=O)n(Cc2ccc(Cl)cc2Cl)cc1F] | yellow oil | | ESIMS m/z 343 ([M + H]$^+$) | (CDCl$_3$) 8.81 (s, 1H), 7.40 (d, J = 2.3 Hz, 1H), 7.37 (d, J = 8.2 Hz, 1H), 7.33 (d, J = 5.6 Hz, 1H), 7.22 (dd, J = 8.2, 2.3 Hz, 1H), 5.06 (s, 2H), 3.18 (s, 6H) |

TABLE I-continued

Compounds and Related Characterization Data

| Cmpd | Structure | Appearance | mp (° C.) | MS | ¹H NMR[a] (δ, solvent) |
|---|---|---|---|---|---|
| 6 | 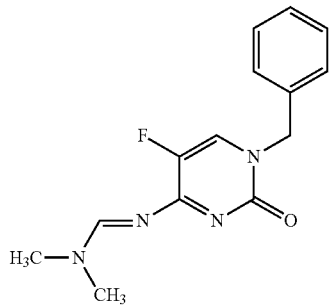 [SMILES: CN(C)/C=N/c1nc(=O)n(Cc2ccccc2)cc1F] | white solid | 186-188 | ESIMS m/z 275 ([M + H]+) | (CDCl$_3$) 8.85 (s, 1H), 7.41-7.31 (m, 5H), 7.24 (d, J = 5.5 Hz, 1H), 5.04 (s, 2H), 3.22 (s, 1H), 3.21 (s, 3H) |
| 7 | 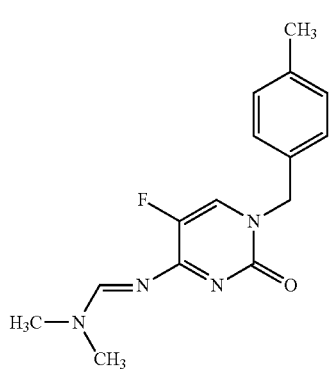 [SMILES: Cc1ccc(Cn2cc(F)c(/N=C/N(C)C)nc2=O)cc1] | white solid | 178-179 | ESIMS m/z 289 ([M + H]+) | (CDCl$_3$) 8.85 (s, 1H), 7.26-7.17 (m, 5H), 4.99 (s, 2H), 3.21 (s, 6H), 2.37 (s, 3H) |
| 13 | 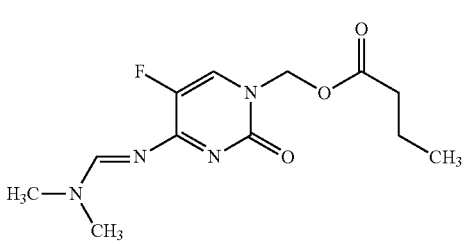 [SMILES: CCCC(=O)OCn1cc(F)c(/N=C/N(C)C)nc1=O] | white solid | 109-111 | ESIMS m/z 285 ([M + H]+) | (600 MHz, DMSO-d$_6$) 8.65 (s, 1H), 8.04 (d, J = 6.2 Hz, 1H), 5.58 (s, 2H), 3.20 (s, 3H), 3.07 (s, 3H), 2.27 (t, J = 7.3 Hz, 2H), 1.53-1.46 (m, 2H), 0.83 (t, J = 7.3 Hz, 3H) |
| 16 | 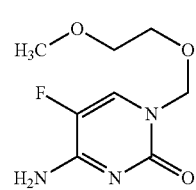 | white solid | 160-163 | ESIMS m/z 218 ([M + H]+) | (DMSO-d$_6$) 7.97 (d, J = 6.6 Hz, 1H), 7.83 (s, 1H), 7.58 (s, 1H), 5.03 (s, 2H), 3.65-3.53 (m, 2H), 3.46-3.38 (m, 2H), 3.22 (s, 3H) |
| 17 | 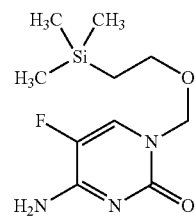 | off-white solid | 187-192 | ESIMS m/z 260 ([M + H]+) | (DMSO-d$_6$) δ 7.96 (d, J = 6.6 Hz, 1H), 7.80 (s, 1H), 7.57 (s, 1H), 4.99 (s, 2H), 3.51 (dd, J = 20.2, 12.2 Hz, 2H), 0.85 (t, J = 7.9 Hz, 2H), −0.03 (s, 9H). |
| 18 | 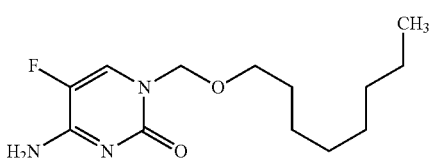 | off-white solid | 166-170 | ESIMS m/z 272 ([M + H]+) | (DMSO-d$_6$) 7.98 (d, J = 6.5 Hz, 1H), 7.85 (s, 1H), 7.62 (s, 1H), 5.01 (s, 2H), 3.44 (t, J = 6.4 Hz, 2H), 1.47 (m, 2H), 1.24 (m, 10H), 0.86 (t, J = 5.9 Hz, 3H). |

TABLE I-continued

Compounds and Related Characterization Data

| Cmpd | Structure | Appearance | mp (° C.) | MS | ¹H NMR[a] (δ, solvent) |
|---|---|---|---|---|---|
| 19 | 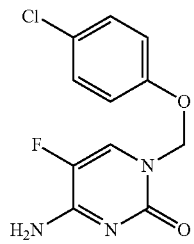 [SMILES: Nc1nc(=O)n(COc2ccc(Cl)cc2)cc1F] | white | 240-245 | ESIMS m/z 270 ([M + H]⁺) | (DMSO-d₆) 8.09 (d, J = 6.6 Hz, 1H), 7.97 (s, 1H), 7.72 (s, 1H), 7.36 (d, J = 8.8 Hz, 2H), 7.07 (d, J = 8.9 Hz, 2H), 5.58 (s, 2H) |
| 20 | 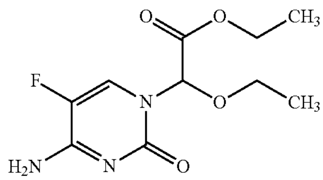 [SMILES: CCOC(=O)C(OCC)n1cc(F)c(N)nc1=O] | white solid | 150-154 | ESIMS m/z 260 ([M + H]⁺) | (DMSO-d₆) 7.97 (s, 1H), 7.81 (d, J = 6.3 Hz, 1H), 7.72 (s, 1H), 5.84 (s, 1H), 4.15 (dd, J = 13.7, 6.8 Hz, 2H), 3.59 (dd, J = 13.3, 6.4 Hz, 2H), 1.28-1.04 (m, 6H) |
| 21 | 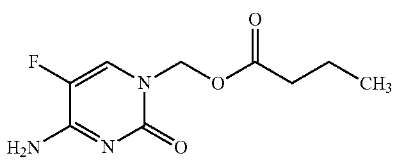 [SMILES: CCCC(=O)OCn1cc(F)c(N)nc1=O] | white solid | 210-214 | ESIMS m/z 230 ([M + H]⁺) | (DMSO-d₆) 7.99 (m, J = 6.7 Hz, 2H), 7.72 (s, 1H), 5.55 (s, 2H), 2.30 (t, J = 7.2 Hz, 2H), 1.68-1.39 (m, 2H), 0.86 (t, J = 7.4 Hz, 3H) |
| 22 | 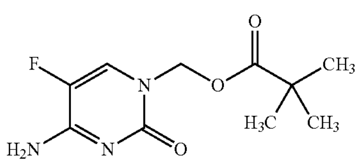 [SMILES: CC(C)(C)C(=O)OCn1cc(F)c(N)nc1=O] | white solid | 259-264 | ESIMS m/z 244 ([M + H]⁺) | (DMSO-d₆) 7.99 (d, J = 6.7 Hz, 1H), 7.97 (s, 1H), 7.71 (s, 1H), 5.54 (s, 2H), 1.12 (s, 9H) |
| 23 | 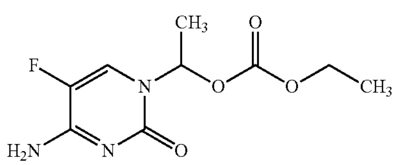 [SMILES: CCOC(=O)OC(C)n1cc(F)c(N)nc1=O] | white solid | 162-166 | ESIMS m/z 246 ([M + H]⁺) | (DMSO-d₆) 8.08 (d, J = 7.0 Hz, 1H), 7.95 (s, 1H), 7.69 (s, 1H), 6.72 (q, J = 5.2 Hz, 1H), 4.12 (q, J = 7.0 Hz, 2H), 1.55 (d, J = 6.1 Hz, 3H), 1.20 (t, J = 7.1 Hz, 3H) |
| 29 | 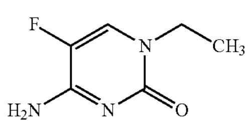 | white solid | 279 dec | ESIMS m/z 158 ([M + H]⁺) | (DMSO-d₆) 7.98 (d, J = 6.8 Hz, 1H), 7.57 (s, 1H), 7.39 (s, 1H), 3.63 (q, J = 7.1 Hz, 2H), 1.14 (t, J = 7.1 Hz, 3H) |
| 30 | 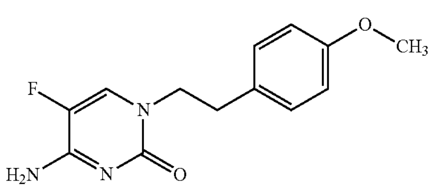 [SMILES: COc1ccc(CCn2cc(F)c(N)nc2=O)cc1] | white solid | 168-189 | ESIMS m/z 264 ([M + H]⁺) | (DMSO-d₆) 7.93 (d, J = 3.3 Hz, 1H), 7.31 (s, 1H), 7.19 (d, J = 8.6 Hz, 2H), 6.90-6.82 (m, 2H), 4.28 (t, J = 6.9 Hz, 2H), 3.72 (s, 3H), 2.89 (t, J = 6.9 Hz, 2H) |
| 31 | 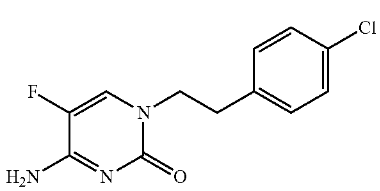 [SMILES: Nc1nc(=O)n(CCc2ccc(Cl)cc2)cc1F] | white solid | 252-254 | ESIMS m/z 268 ([M + H]⁺) | (DMSO-d₆) 7.97 (d, J = 3.5 Hz, 1H), 7.46 (s, 2H), 7.39-7.34 (m, 2H), 7.34-7.28 (m, 2H), 4.34 (t, J = 6.7 Hz, 2H), 2.97 (t, J = 6.7 Hz, 2H) |

TABLE I-continued

Compounds and Related Characterization Data

| Cmpd | Structure | Appearance | mp (° C.) | MS | $^1$H NMR$^a$ ($\delta$, solvent) |
|---|---|---|---|---|---|
| 32 | 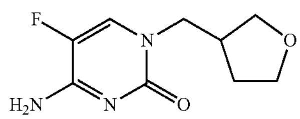 | pale yellow solid | 255 dec | ESIMS m/z 214 ([M + H]$^+$) | (DMSO-d$_6$) 7.92 (d, J = 3.2 Hz, 1H), 7.27 (s, 2H), 4.10 (dd, J = 10.5, 6.7 Hz, 1H), 4.02 (dd, J = 10.5, 8.0 Hz, 1H), 3.78-3.69 (m, 2H), 3.63 (dd, J = 15.0, 7.8 Hz, 1H), 3.47 (dd, J = 8.6, 5.6 Hz, 1H), 2.59 (dt, J = 14.1, 7.2 Hz, 1H), 1.97 (dtd, J = 13.8, 8.2, 5.6 Hz, 1H), 1.65-1.53 (m, 1H) |
| 33 | 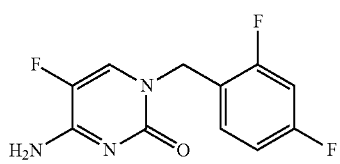 [SMILES: Nc1nc(=O)n(Cc2ccc(F)cc2F)cc1F] | beige solid | 250-254 | ESIMS m/z 256 ([M + H]$^+$) | (DMSO-d$_6$.) 8.04 (d, J = 6.6 Hz, 1H), 7.74 (s, 1H), 7.50 (s, 1H), 7.35-7.20 (m, 2H), 7.06 (td, J = 8.5, 1.8 Hz, 1H), 4.82 (s, 2H) |
| 35 | 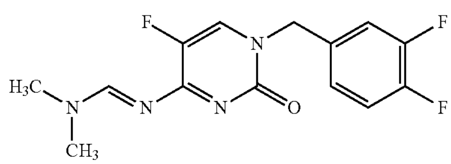 [SMILES: CN(C)/C=N/c1nc(=O)n(Cc2ccc(F)c(F)c2)cc1F] | white solid | 196-200 | ESIMS m/z 311 ([M + H]$^+$) | (DMSO-d$_6$) 8.64 (s, 1H), 8.24 (d, J = 6.2 Hz, 1H), 7.48-7.35 (m, 2H), 7.23-7.13 (m, 1H), 4.85 (s, 2H), 3.21 (s, 3H), 3.08 (s, 3H) |
| 36 | 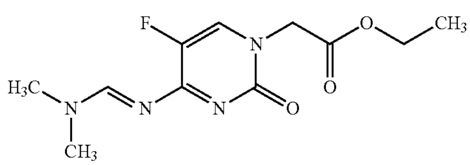 [SMILES: CCOC(=O)Cn1cc(F)c(/N=C/N(C)C)nc1=O] | white solid | 196-199 | ESIMS m/z 271 ([M + H]$^+$) | (DMSO-d$_6$) 8.67 (s, 1H), 8.05 (d, J = 6.2 Hz, 1H), 4.48 (s, 2H), 4.14 (q, J = 7.1 Hz, 2H), 3.22 (s, 3H), 3.10 (s, 3H), 1.20 (t, J = 7.1 Hz, H) |
| 40 | 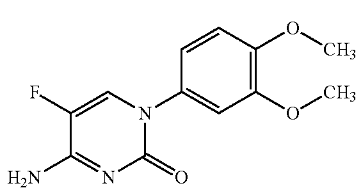 [SMILES: COc1ccc(-n2cc(F)c(N)nc2=O)cc1OC] | white solid | 244.8-245.6 | ESIMS m/z 266 ([M + H]$^+$) | (DMSO-d6) 7.98 (d, J = 6.7 Hz, 1H), 7.80 (s, 1H), 7.57 (s, 1H), 7.00 (m, 2H), 6.89 (dd, J = 8.6, 2.3 Hz, 1H), 3.79 (s, 3H), 3.76 (s, 3H) |
| 41 | 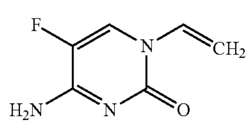 | white solid | 213.5-214.4 | ESIMS m/z 156 ([M + H]$^+$) | (DMSO-d$_6$) 8.28 (d, J = 7.1 Hz, 1H), 8.01 (s, 1H), 7.77 (s, 1H), 7.18 (dd, J = 15.4, 10.3 Hz, 1H), 5.27 (d, J = 16.2 Hz, 1H), 4.78 (d, J = 8.0 Hz, 1H) |
| 42 | 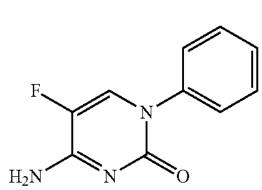 [SMILES: Nc1nc(=O)n(-c2ccccc2)cc1F] | off-white solid | 233-235 | ESIMS m/z 206 ([M + H]$^+$) | (DMSO-d$_6$) 8.05 (dd, J = 6.8, 1.7 Hz, 1H), 7.86 (s, 1H), 7.62 (s, 1H), 7.51-7.31 (m, 5H) |

TABLE I-continued

Compounds and Related Characterization Data

| Cmpd | Structure | Appearance | mp (° C.) | MS | $^1$H NMR$^a$ ($\delta$, solvent) |
|---|---|---|---|---|---|
| 43 | 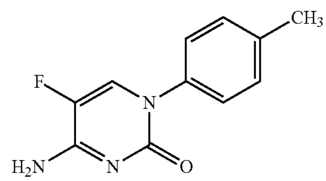 [SMILES: Cc1ccc(-n2cc(F)c(N)nc2=O)cc1] | off-white solid | 225-227 | ESIMS m/z 220 ([M + H]$^+$) | (DMSO-d$_6$) 8.00 (d, J = 6.7 Hz, 1H), 7.83 (s, 1H), 7.59 (s, 1H), 7.25 (s, 4H), 2.34 (s, 3H) |
| 44 | 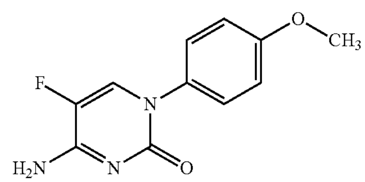 [SMILES: COc1ccc(-n2cc(F)c(N)nc2=O)cc1] | brown solid | 230-232 | ESIMS m/z 236 ([M + H]$^+$) | (DMSO-d$_6$) 7.99 (d, J = 6.7 Hz, 1H), 7.81 (s, 1H), 7.57 (s, 1H), 7.29 (d, J = 8.8 Hz, 2H), 6.98 (d, J = 8.8 Hz, 2H), 3.78 (s, J = 8.6 Hz, 3H) |
| 45 | 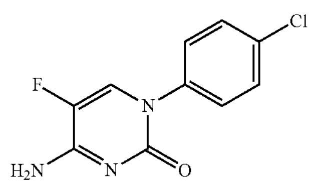 [SMILES: Nc1nc(=O)n(-c2ccc(Cl)cc2)cc1F] | off-white solid | 255-257 | ESIMS m/z 240 ([M + H]$^+$) | (DMSO-d$_6$) 8.07 (d, J = 6.3 Hz, 1H), 7.93 (s, 1H), 7.68 (s, 1H), 7.51 (dd, J = 8.6, 1.0 Hz, 2H), 7.43 (dd, J = 8.7, 1.1 Hz, 2H) |
| 46 | 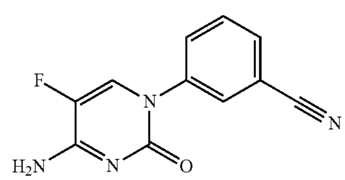 [SMILES: N#Cc1cccc(-n2cc(F)c(N)nc2=O)c1] | pale brown solid | 175-178 | ESIMS m/z 231 ([M + H]$^+$) | (DMSO-d$_6$) 8.16 (d, J = 6.9 Hz, 1H), 7.98-7.94 (m, 1H), 7.86-7.82 (m, 1H), 7.82-7.76 (m, 1H), 7.67 (d, J = 8.0 Hz, 1H) |
| 47 | 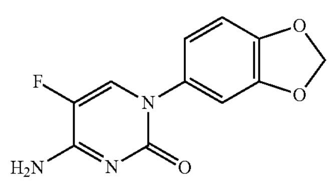 [SMILES: Nc1nc(=O)n(-c2ccc3c(c2)OCO3)cc1F] | off-white solid | 275-279 | ESIMS m/z 250 ([M + H]$^+$) | (DMSO-d$_6$) 7.96 (d, J = 6.7 Hz, 1H), 7.82 (s, 1H), 7.57 (s, 1H), 6.99 (d, J = 2.1 Hz, 1H), 6.96 (d, J = 8.2 Hz, 1H), 6.82 (dd, J = 8.3, 2.1 Hz, 1H), 6.08 (s, 2H) |
| 48 | 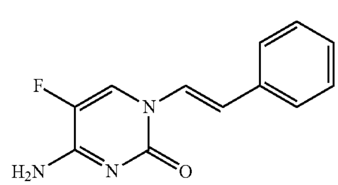 [SMILES: Nc1nc(=O)n(/C=C/c2ccccc2)cc1F] | yellow solid | 256-258 | ESIMS m/z 232 ([M + H]$^+$) | (DMSO-d$_6$) $\delta$ 8.42 (d, J = 7.2 Hz, 1H), 8.04 (s, 1H), 7.82 (s, 1H), 7.66 (d, J = 15.0 Hz, 1H), 7.44 (d, J = 7.9 Hz, 2H), 7.36 (t, J = 7.6 Hz, 2H), 7.26 (dd, J = 10.5, 4.0 Hz, 1H), 6.81 (d, J = 15.0 Hz, 1H) |
| 49 | 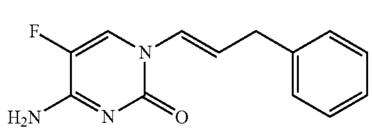 [SMILES: Nc1nc(=O)n(/C=C/Cc2ccccc2)cc1F] | pale-brown solid | 212-214 | ESIMS m/z 246 ([M + H]$^+$) | (DMSO-d$_6$) 8.24 (d, J = 7.2 Hz, 1H), 7.92 (s, 1H), 7.69 (s, 1H), 7.31 (m, 2H), 7.22 (dd, J = 14.9, 7.1 Hz, 3H), 7.03 (dd, J = 14.5, 1.6 Hz, 1H), 5.95 (dt, J = 14.5, 7.3 Hz, 1H), 3.45 (d, J = 7.1 Hz, 2H) |

TABLE I-continued

Compounds and Related Characterization Data

| Cmpd | Structure | Appearance | mp (° C.) | MS | ¹H NMR$^a$ (δ, solvent) |
|---|---|---|---|---|---|
| 50 | 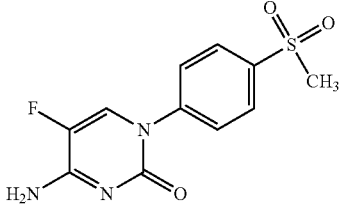 [SMILES: CS(=O)(=O)c1ccc(-n2cc(F)c(N)nc2=O)cc1] | off-white solid | 244.4-245.7 | ESIMS m/z 284 ([M + H]$^+$) | (DMSO-d$_6$) 8.14 (d, J = 6.8 Hz, 1H), 8.04-7.92 (m, 3H), 7.75 (s, J = 7.8 Hz, 1H), 7.69 (d, J = 8.4 Hz, 2H), 3.26 (s, 3H). |
| 51 | 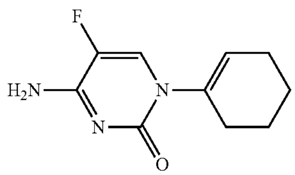 [SMILES: Nc1nc(=O)n(C2=CCCCC2)cc1F] | white solid | 190.6-192.7 | ESIMS m/z 210 ([M + H]$^+$) | (DMSO-d$_6$) 7.75 (d, J = 6.6 Hz, 1H), 7.62 (s, 1H), 7.41 (s, 1H), 5.66 (t, J = 3.7 Hz, 1H), 2.15 (d, J = 36.9 Hz, 4H), 1.60 (dt, J = 10.5, 5.0 Hz, 4H) |
| 52 | 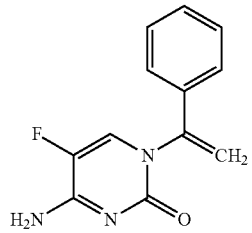 [SMILES: C=C(c1ccccc1)n1cc(F)c(N)nc1=O] | yellow solid | 211.2-213.0 | ESIMS m/z 232 ([M + H]$^+$) | (DMSO-d$_6$) 7.97 (d, J = 6.5 Hz, 1H), 7.83 (s, 1H), 7.60 (s, 1H), 7.45-7.24 (m, 5H), 5.86 (d, J = 0.9 Hz, 1H), 5.37 (d, J = 0.9 Hz, 1H) |
| 53 | 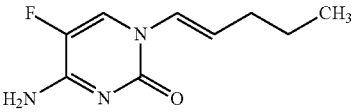 | white solid | 152.8-153.4 | ESIMS m/z 198 ([M + H]$^+$) | (DMSO-d$_6$) 8.17 (d, J = 7.1 Hz, 1H), 7.85 (s, 1H), 7.62 (s, 1H), 6.88 (d, J = 14.5 Hz, 1H), 5.74 (dt, J = 14.3, 7.1 Hz, 1H), 2.06 (q, J = 7.1 Hz, 2H), 1.48-1.31 (m, 2H), 0.89 (t, J = 7.3 Hz, 3H) |
| 54 | 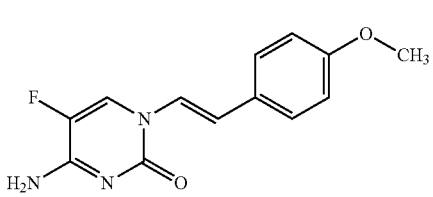 [SMILES: COc1ccc(/C=C/n2cc(F)c(N)nc2=O)cc1] | yellow solid | 263.3-265.1 | ESIMS m/z 262 ([M + H]$^+$) | (CD$_3$OD) 8.20 (d, J = 6.7 Hz, 1H), 7.55 (dd, J = 14.8, 1.9 Hz, 1H), 7.40 (d, J = 8.7 Hz, 2H), 6.94-6.87 (m, 2H), 6.68 (d, J = 14.7 Hz, 1H), 3.80 (s, 3H) |
| 55 | 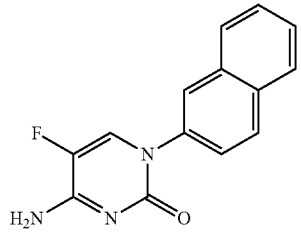 | white solid | 272.8-274.2 | ESIMS m/z 256 ([M + H]$^+$) | (DMSO-d$_6$) 8.17 (d, 7 = 6.7 Hz, 1H), 8.00-7.85 (m, 5H), 7.65 (s, 1H), 7.61-7.49 (m, 3H) |

TABLE I-continued

Compounds and Related Characterization Data

| Cmpd | Structure | Appearance | mp (° C.) | MS | $^1$H NMR$^a$ ($\delta$, solvent) |
|---|---|---|---|---|---|
| 57 | 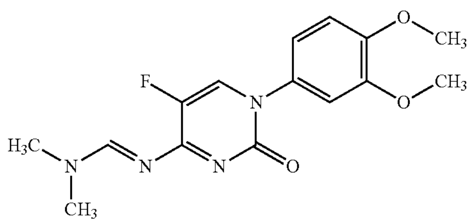 | yellow solid | 196.1-198.0 | ESIMS m/z 321 ([M + H]$^+$) | (DMSO-d$_6$) 8.72 (s, 1H), 8.09 (d, J = 6.2 Hz, 1H), 7.07-7.02 (m, 1H), 7.00 (s, 1H), 6.94 (dd, J = 8.5, 2.3 Hz, 1H), 3.80 (s, 3H), 3.77 (s, 3H), 3.25 (s, 3H), 3.13 (s, 3H) |
| 58 | 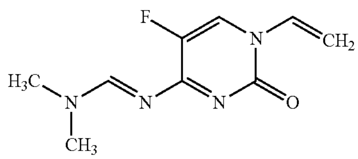 | yellow solid | 179.6-181.3 | ESIMS m/z 211 ([M + H]$^+$) | (DMSO-d$_6$) 8.69 (d, J = 17.4 Hz, 1H), 8.37 (d, J = 6.6 Hz, 1H), 7.21 (ddd, J = 22.7, 11.3, 6.8 Hz, 1H), 5.41 (d, J = 16.2 Hz, 1H), 4.89 (d, J = 9.2 Hz, 1H), 3.25 (s, 3H), 3.11 (d, J = 11.5 Hz, 3H) |
| 59 | 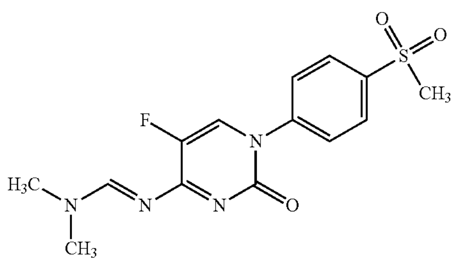 [SMILES: CN(C)/C=N/c1nc(=O)n(-c2ccc(S(C)(=O)=O)cc2)cc1F] | white solid | 284.6-186.9 | ESIMS m/z 339 ([M + H]$^+$) | (DMSO-d$_6$) 8.75 (s, 1H), 8.23 (d, J = 6.3 Hz, 1H), 8.01 (d, J = 8.6 Hz, 2H), 7.74 (d, J = 8.6 Hz, 2H), 3.27 (s, 3H), 3.26 (s, 3H), 3.14 (s, 3H) |
| 60 | 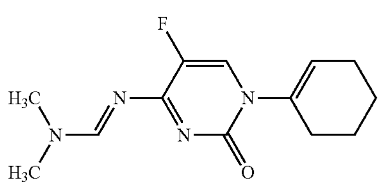 [SMILES: CN(C)/C=N/c1nc(=O)n(C2=CCCCC2)cc1F] | white solid | 173.2-174.4 | ESIMS m/z 265 ([M + H]$^+$) | (DMSO-d$_6$) 8.63 (s, 1H), 7.87 (d, J = 6.0 Hz, 1H), 5.72 (s, 1H), 3.21 (s, 3H), 3.08 (s, 3H), 2.18 (d, J = 37.4 Hz, 4H), 1.62 (dd, J = 29.1, 4.7 Hz, 4H) |
| 61 | 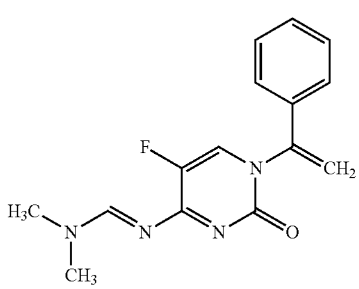 [SMILES: C=C(c1ccccc1)n1cc(F)c(/N=C/N(C)C)nc1=O] | yellow solid | 147.0-147.9 | ESIMS m/z 287 ([M + H]$^+$) | (DMSO-d$_6$) 8.69 (s, 1H), 8.08 (d, J = 6.0 Hz, 1H), 7.40-7.27 (m, 5H), 5.92 (d, J = 1.2 Hz, 1H), 5.44 (d, J = 1.1 Hz, 1H), 3.23 (s, 3H), 3.12 (s, 3H) |
| 62 | 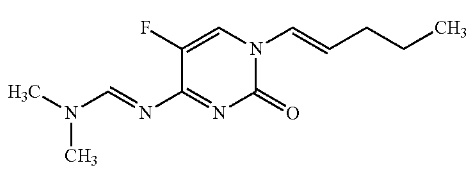 [SMILES: CCC/C=C/n1cc(F)c(/N=C/N(C)C)nc1=O] | white solid | 144.7-146.3 | ESIMS m/z 253 ([M + H]$^+$) | (CD$_3$OD) 8.72 (s, 1H), 8.06 (d, J = 6.0 Hz, 1H), 6.96 (dd, J = 14.3, 1.6 Hz, 1H), 5.89 (dt, J = 14.4, 7.2 Hz, 1H), 3.27 (s, 3H), 3.21 (s, 3H), 2.18 (ddd, J = 14.7, 7.3, 1.4 Hz, 2H), 1.59-1.44 (m, 2H), 0.98 (t, J = 7.4 Hz, 3H) |

TABLE I-continued

Compounds and Related Characterization Data

| Cmpd | Structure | Appearance | mp (° C.) | MS | $^1$H NMR$^a$ (δ, solvent) |
|---|---|---|---|---|---|
| 63 | 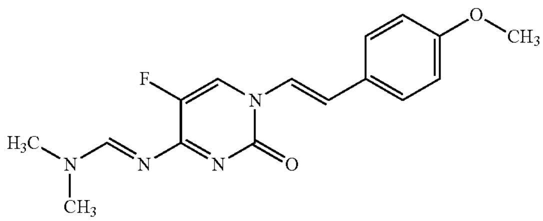 | yellow solid | 264.3-265.3 | ESIMS m/z 317 ([M + H]$^+$) | DMSO-d$_6$) 8.72 (s, 1H), 8.44 (d, J = 6.8 Hz, 1H), 7.56 (dd, J = 14.9, 1.8 Hz, 1H), 7.40 (d, J = 8.7 Hz, 2H), 6.93 (d, J = 8.7 Hz, 2H), 6.86 (d, J = 14.9 Hz, 1H), 3.76 (s, 3H), 3.25 (s, 3H), 3.12 (s, 3H) |
| 64 | 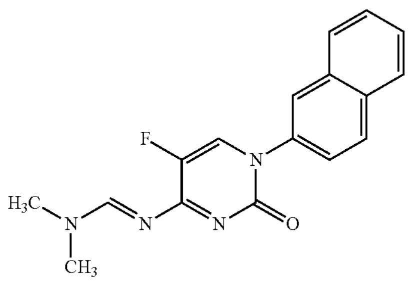 [SMILES: CN(C)/C=N/c1nc(=O)n(-c2ccc3ccccc3c2)cc1F] | yellow solid | 222.4-224.4 | ESIMS m/z 311 ([M + H]$^+$) | (DMSO-d$_6$) 8.74 (s, 1H), 8.27 (d, J = 6.2 Hz, 1H), 8.04-7.90 (m, 4H), 7.65-7.49 (m, 3H), 3.25 (s, 3H), 3.13 (s, 3H) |
| 66 | 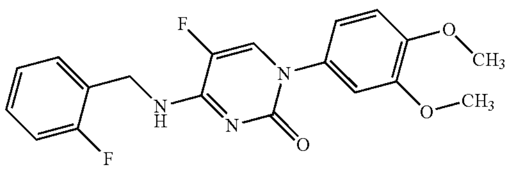 [SMILES: COc1ccc(-n2cc(F)c(NCc3ccccc3F)nc2=O)cc1OC] | white solid | 206.3-207.9 | ESIMS m/z 374 ([M + H]$^+$) | (DMSO-d$_6$) 8.60 (t, J = 6.0 Hz, 1H), 8.03 (d, J = 6.8 Hz, 1H), 7.43-7.29 (m, 2H), 7.26-7.16 (m, J = 12.8, 5.9 Hz, 2H), 7.03-6.97 (m, 2H), 6.90 (dd, J = 8.5, 2.0 Hz, 1H), 4.63 (d, J = 5.7 Hz, 2H), 3.79 (s, 3H), 3.75 (s, 3H) |
| 67 | 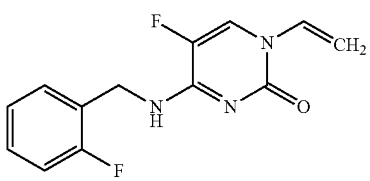 [SMILES: C=Cn1cc(F)c(NCc2ccccc2F)nc1=O] | white solid | 168.6-169.1 | ESIMS m/z 264 ([M + H]$^+$) | (DMSO-d$_6$) 8.81 (s, 1H), 8.32 (d, J = 7.3 Hz, 1H), 7.34 (dd, J = 14.4, 6.6 Hz, 2H), 7.27-7.09 (m, 2H), 5.30 (dd, J = 16.1, 1.5 Hz, 1H), 4.80 (dd, J = 9.2, 1.5 Hz, 1H), 4.62 (d, J = 5.8 Hz, 2H) |
| 68 | 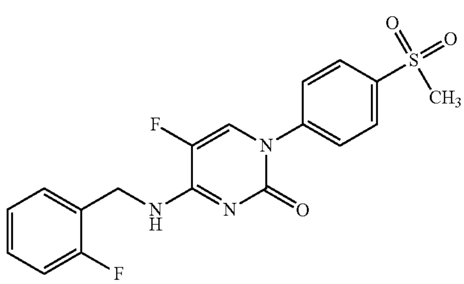 [SMILES: CS(=O)(=O)c1ccc(-n2cc(F)c(NCc3ccccc3F)nc2=O)cc1] | white solid | 231.6-233.1 | ESIMS m/z 392 ([M + H]$^+$) | (CD$_3$OD) 8.11-8.00 (m, 2H), 7.94 (d, J = 6.3 Hz, 1H), 7.76-7.66 (m, 2H), 7.47 (t, J = 6.9 Hz, 1H), 7.37-7.25 (m, 1H), 7.20-7.04 (m, 2H), 4.78 (s, 2H), 3.16 (s, 3H) |
| 69 | 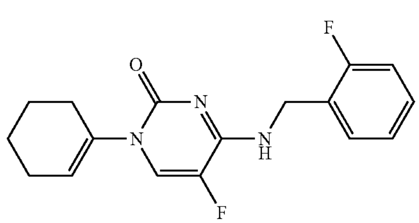 [SMILES: O=c1nc(NCc2ccccc2F)c(F)cn1C1=CCCCC1] | white solid | 151.5-152.6 | ESIMS m/z 318 ([M + H]$^+$) | (DMSO-d$_6$) 8.45 (t, J = 5.7 Hz, 1H), 7.80 (d, J = 6.7 Hz, 1H), 7.37-7.10 (m, 4H), 5.68 (s, 1H), 4.57 (d, J = 5.8 Hz, 2H), 2.15 (d, J = 33.7 Hz, 4H), 1.75-1.47 (m, 4H) |

TABLE I-continued

Compounds and Related Characterization Data

| Cmpd | Structure | Appearance | mp (° C.) | MS | $^1$H NMR$^a$ ($\delta$, solvent) |
|---|---|---|---|---|---|
| 70 | 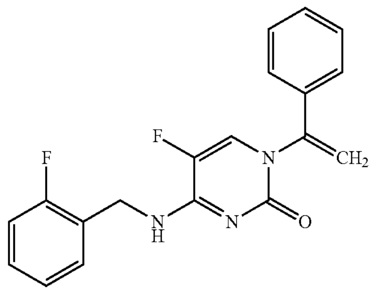 [SMILES: C=C(c1ccccc1)n1cc(F)c(NCc2ccccc2F)nc1=O] | white solid | 138.9-140.2 | ESIMS m/z 340 ([M + H]$^+$) | (DMSO-d$_6$) 8.63 (t, J = 5.9 Hz, 1H), 8.02 (d, J = 6.6 Hz, 1H), 7.46-7.25 (m, 7H), 7.25-7.12 (m, 2H), 5.89 (d, J = 0.9 Hz, 1H), 5.39 (d, J = 0.9 Hz, 1H), 4.62 (d, J = 5.8 Hz, 2H) |
| 71 | 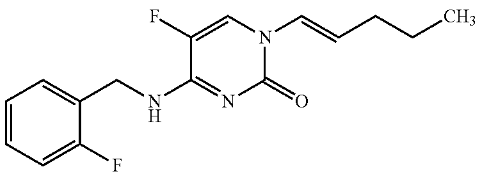 [SMILES: CCC/C=C/n1cc(F)c(NCc2ccccc2F)nc1=O] | white oil | | ESIMS m/z 306 ([M + H]$^+$) | (DMSO-d$_6$) 8.68 (t, J = 5.7 Hz, 1H), 8.22 (d, J = 7.2 Hz, 1H), 7.39-7.23 (m, J = 7.5 Hz, 2H), 7.23-7.05 (m, J = 15.2, 8.1 Hz, 2H), 6.88 (d, J = 14.4 Hz, 1H), 5.76 (dt, J = 14.4, 7.2 Hz, 1H), 4.60 (d, J = 5.8 Hz, 2H), 2.06 (dd, J = 14.3, 7.1 Hz, 2H), 1.48-1.29 (m, 2H), 0.89 (t, J = 7.3 Hz, 3H) |
| 72 | 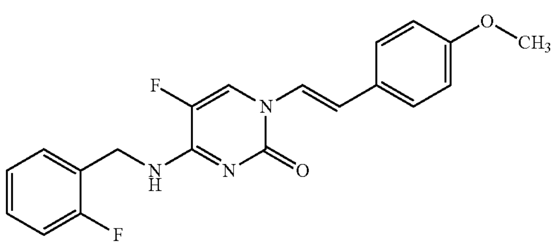 [SMILES: COc1ccc(/C=C/n2cc(F)c(NCc3ccccc3F)nc2=O)cc1] | yellow solid | 196.8-198.5 | ESIMS m/z 370 ([M + H]$^+$) | (CD$_3$OD) 8.18 (d, J = 6.8 Hz, 1H), 7.56 (dd, J = 14.8, 2.0 Hz, 1H), 7.50-7.36 (m, 3H), 7.35-7.24 (m, 1H), 7.14 (dd, J = 7.6, 6.4 Hz, 1H), 7.10-7.03 (m, 2H), 6.90 (d, J = 8.8 Hz, 2H), 6.68 (d, J = 14.7 Hz, 1H), 4.76 (s, 2H), 3.80 (s, 3H) |
| 73 | 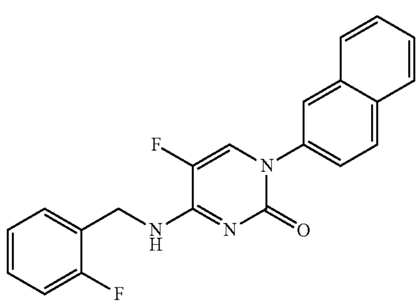 [SMILES: O=c1nc(NCc2ccccc2F)c(F)cn1-c1ccc2ccccc2c1] | white solid | 207.5-209.0 | ESIMS m/z 364 ([M + H]$^+$) | (DMSO-d$_6$) 8.76-8.60 (m, 1H), 8.21 (d, J = 6.8 Hz, 1H), 8.01-7.87 (m, 4H), 7.64-7.47 (m, 3H), 7.10-7.45 (m, 4H), 4.65 (d, J = 6.2 Hz, 2H) |
| 75 | 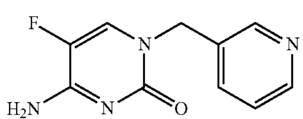 | brown solid | 292.2-231.3 | ESIMS m/z 221 ([M + H]$^+$) | (CD$_3$OD) 8.58 (d, J = 2.0 Hz, 1H), 8.49 (dd, J = 4.9, 1.5 Hz, 1H), 7.98 (d, J = 6.2 Hz, 1H), 7.90-7.82 (m, 1H), 7.44 (dd, J = 7.9, 4.9 Hz, 1H), 4.98 (s, 2H) |

TABLE I-continued

Compounds and Related Characterization Data

| Cmpd | Structure | Appearance | mp (° C.) | MS | ¹H NMR$^a$ (δ, solvent) |
|---|---|---|---|---|---|
| 76 | (5-fluoro-1-((tetrahydrofuran-2-yl)methyl)cytosine) | off-white solid | 179.2-181.1 | ESIMS m/z 214 ([M + H]$^+$) | (DMSO-d$_6$) 7.83 (d, J = 6.8 Hz, 1H), 7.58 (s, 1H), 7.37 (s, 1H), 4.08-3.98 (m, 1H), 3.84-3.71 (m, 2H), 3.63 (dd, J = 14.3, 7.3 Hz, 1H), 3.50 (dd, J = 13.5, 7.8 Hz, 1H), 1.98-1.72 (m, 3H), 1.61-1.43 (m, 1H) |
| 77 | (5-fluoro-1-isobutylcytosine) | white solid | 140-142.8 | ESIMS m/z 186 ([M + H]$^+$) | (DMSO-d$_6$) 8.57 (d, J = 6.8 Hz, 1H), 8.15 (s, 1H), 7.98 (s, 1H), 4.06 (d, J = 7.4 Hz, 2H), 2.72-2.54 (m, 1H), 1.47 (d, J = 6.6 Hz, 6H) |
| 78 | (5-fluoro-1-(2-ethoxyethyl)cytosine) | off-white solid | 207.3-208.2 | ESIMS m/z 202 ([M + H]$^+$) | (CDCl$_3$) 7.56 (d, J = 5.3 Hz, 1H), 3.99-3.91 (m, 2H), 3.68-3.62 (m, 2H), 3.48 (q, J = 7.0 Hz, 2H), 1.17 (t, J = 7.0 Hz, 3H) |
| 79 | (5-fluoro-1-((methylthio)methyl)cytosine) | off-white solid | 128.5-130.6 | ESIMS m/z 190 ([M + H]$^+$), 188 ([M − H]$^−$) | (CD$_3$OD) 7.52 (d, J = 5.8 Hz, 1H), 4.59 (s, 2H), 2.21 (s, 3H) |
| 81 | (benzyl (1-(cyclopropylmethyl)-5-fluoro-2-oxopyrimidin-4-yl)carbamate) | off-white solid | 228-230 | ESIMS m/z 318 ([M + H]$^+$), | (CD$_3$OD) 8.22 (s, 1H), 7.54-7.25 (m, 5H), 5.26 (s, 2H), 3.71 (d, J = 6.4 Hz, 2H), 1.30 (s, 1H), 0.68-0.53 (m, 2H), 0.50-0.33 (m, 2H) |
| 82 | (diphenyl imidodicarbonate derivative) | off-white solid | 159-161 | ESIMS m/z 424 ([M + H]$^+$) | (CD$_3$OD) 8.72 (d, J = 4.9 Hz, 1H), 7.52-7.41 (m, 4H), 7.36-7.31 (m, 2H), 7.28-7.23 (m, 4H), 3.87 (d, J = 7.3 Hz, 2H), 1.41-1.33 (m, 1H), 0.71-0.63 (m, 2H), 0.53-0.45 (m, 2H) |
| 83 | (ethyl (5-fluoro-2-oxo-1-(pyridin-3-ylmethyl)pyrimidin-4-yl)carbamate) | gum | | ESIMS m/z 293 ([M + H]$^+$) | (CD$_3$OD) 8.62 (d, J = 1.6 Hz, 1H), 8.51 (dd, J = 4.9, 1.3 Hz, 1H), 8.29 (d, J = 5.3 Hz, 1H), 7.90 (d, J = 7.8 Hz, 1H), 7.45 (dd, J = 8.0, 4.9 Hz, 1H), 5.06 (s, 2H), 4.25 (q, J = 7.1 Hz, 2H), 1.32 (t, J = 7.1 Hz, 3H) |

TABLE I-continued

Compounds and Related Characterization Data

| Cmpd | Structure | Appearance | mp (° C.) | MS | $^1$H NMR$^a$ ($\delta$, solvent) |
|---|---|---|---|---|---|
| 84 | 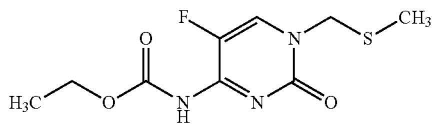 [SMILES: CCOC(=O)Nc1nc(=O)n(CSC)cc1F] | off-white solid | 137.1-138.8 | ESIMS m/z 260 ([M − H]$^-$) | (Acetone-d$_6$) 8.18 (s, 1H), 8.00 (d, J = 7.2 Hz, 1H), 4.64 (d, J = 6.3 Hz, 2H), 4.37 (q, J = 7.1 Hz, 2H), 2.23 (d, J = 4.4 Hz, 3H), 1.35 (t, J = 7.1 Hz, 3H) |
| 86 | 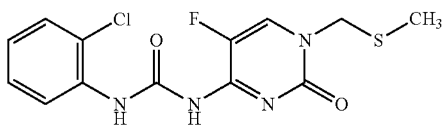 [SMILES: CSCn1cc(F)c(NC(=O)Nc2ccccc2Cl)nc1=O] | yellow solid | 181.8-183.5 | ESIMS m/z 343 ([M + H]$^+$) | (CD$_3$OD) 8.28 (d, J = 5.9 Hz, 1H), 8.22 (dd, J = 8.3, 1.4 Hz, 1H), 7.47 (dd, J = 8.0, 1.4 Hz, 1H), 7.35-7.27 (m, 1H), 7.17-7.09 (m, 1H), 4.98 (s, 2H), 2.23 (s, 3H) |
| 87 | 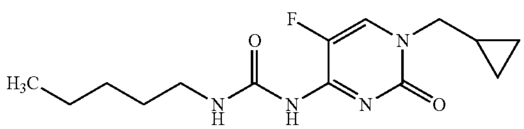 [SMILES: CCCCCNC(=O)Nc1nc(=O)n(CC2CC2)cc1F] | off-white solid | 113.0-114.9 | ESIMS m/z 297 ([M + H]$^+$) | (DMSO) 9.87 (s, 1H), 9.38 (s, 1H), 8.34 (d, J = 5.9 Hz, 1H), 3.56 (d, J = 7.2 Hz, 2H), 3.21 (d, J = 5.8 Hz, 2H), 1.58-1.41 (m, 2H), 1.40-1.09 (m, 5H), 0.88 (t, J = 6.8 Hz, 3H), 0.56-0.41 (m, 2H), 0.41-0.29 (m, 2H) |
| 88 | 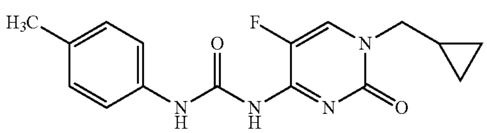 [SMILES: Cc1ccc(NC(=O)Nc2nc(=O)n(CC3CC3)cc2F)cc1] | off-white solid | 205.6-207.5 | ESIMS m/z 317 ([M + H]$^+$) | (CD$_3$OD) 8.25 (d, J = 6.0 Hz, 1H), 7.53 (d, J = 8.4 Hz, 2H), 7.16 (d, J = 8.3 Hz, 2H), 3.75 (d, J = 7.3 Hz, 2H), 2.32 (s, 3H), 1.37-1.26 (m, 1H), 0.67-0.59 (m, 2H), 0.45 (q, J = 4.7 Hz, 2H) |
| 89 | 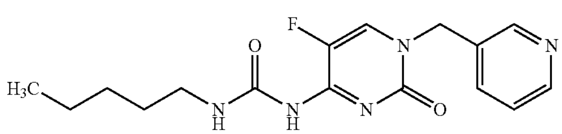 [SMILES: CCCCCNC(=O)Nc1nc(=O)n(Cc2cccnc2)cc1F] | off-white solid | 146.0-147.6 | ESIMS m/z 334 ([M + H]$^+$), | (DMSO-d$_6$) 9.96 (s, 1H), 9.33 (t, J = 5.4 Hz, 1H), 8.59 (d, J = 1.7 Hz, 1H), 8.51 (s, 1H), 8.50 (s, 1H), 7.76 (d, J = 8.0 Hz, 1H), 7.38 (dd, J = 7.6, 4.9 Hz, 1H), 4.93 (s, 1H), 3.20 (dd, J = 12.7, 6.7 Hz, 2H), 1.55-1.38 (m, 2H), 1.29 (dd, J = 8.7, 5.4 Hz, 4H), 0.87 (t, J = 6.7 Hz, 3H) |
| 90 | 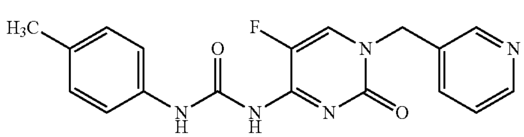 [SMILES: Cc1ccc(NC(=O)Nc2nc(=O)n(Cc3cccnc3)cc2F)cc1] | off-white solid | 178.2-180 | ESIMS m/z 354 ([M + H]$^+$) | (CD$_3$OD) 8.66 (d, J = 1.7 Hz, 1H), 8.52 (dd, J = 4.9, 1.6 Hz, 1H), 8.37 (d, J = 5.9 Hz, 1H), 7.96-7.90 (m, 1H), 7.51 (d, J = 8.5 Hz, 2H), 7.47 (dd, J = 8.2, 5.2 Hz, 1H), 7.15 (d, J = 8.3 Hz, 2H), 5.11 (s, 2H), 2.32 (s, 3H) |

TABLE I-continued

Compounds and Related Characterization Data

| Cmpd | Structure | Appearance | mp (° C.) | MS | $^1$H NMR$^a$ ($\delta$, solvent) |
|---|---|---|---|---|---|
| 91 | 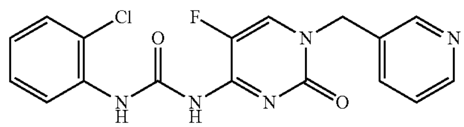 [SMILES: O=C(Nc1ccccc1Cl)Nc1nc(=O)n(Cc2cccnc2)cc1F] | off-white solid | 210.5-212.3 | ESIMS m/z 374 ([M + H]$^+$) | (DMSO-d$_6$) 12.29 (s, 1H), 10.59 (s, 1H), 8.64 (m, 2H), 8.52 (d, J = 4.8 Hz, 1H), 8.31 (dd, J = 8.3, 1.2 Hz, 1H), 7.83-7.77 (m, 1H), 7.52 (dd, J = 8.0, 1.2 Hz, 1H), 7.43-7.31 (m, 2H), 7.12 (td, J = 7.9, 1.5 Hz, 1H), 4.98 (s, 2H) |
| 92 | 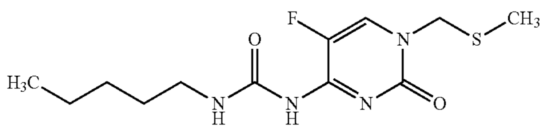 [SMILES: CCCCCNC(=O)Nc1nc(=O)n(CSC)cc1F] | off-white solid | 100.2-101.8 | ESIMS m/z 301 ([M − H]$^−$) | (CD$_3$OD) 8.43 (d, J = 7.4 Hz, 1H), 4.62 (s, 2H), 3.37 (t, J = 7.0 Hz, 2H), 2.22 (s, J = 5.7 Hz, 3H), 1.61 (dd, J = 14.1, 7.1 Hz, 2H), 1.44-1.32 (m, 4H), 0.94 (t, J = 7.0 Hz, 3H) |
| 93 | 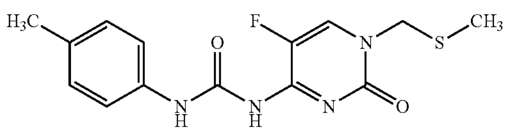 | off-white solid | 188.8-190.2 | ESIMS m/z 323 ([M + H]$^+$) | (CD$_3$OD) 8.27 (d, J = 5.9 Hz, 1H),7.53 (d, J = 8.4 Hz, 2H), 7.16 (d, J = 8.2 Hz, 2H), 5.00 (s, 2H), 2.32 (s, 3H), 2.24 (s, 3H) |
| 95 | 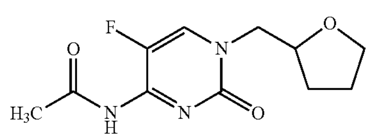 [SMILES: CC(=O)Nc1nc(=O)n(CC2CCCO2)cc1F] | pale yellow gum | | ESIMS m/z 256 ([M + H]$^+$) | (CDCl$_3$) 7.76 (d, J = 5.5 Hz, 1H), 4.30 (dd, J = 13.8, 2.1 Hz, 1H), 4.18 (dd, J = 14.8, 7.6 Hz, 1H), 3.87 (dd, J = 15.2, 6.9 Hz, 1H), 3.78 (dd, J = 14.4, 7.6 Hz, 1H), 3.57 (dd, J = 13.8, 7.9 Hz, 1H), 2.65 (s, 3H), 2.20-2.06 (m, 1H), 2.01-1.85 (m, 2H), 1.58 (ddd, J = 16.1, 12.5, 8.0 Hz, 1H) |
| 96 | 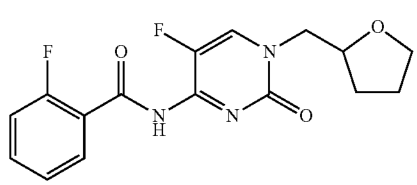 [SMILES: O=C(Nc1nc(=O)n(CC2CCCO2)cc1F)c1ccccc1F] | white solid | 119.8-121.9 | ESIMS m/z 336 ([M + H]$^+$) | (DMSO-d$_6$) 11.22 (s, 1H), 8.38 (s, 1H), 7.70 (s, 1H), 7.63 (dd, J = 13.0, 6.4 Hz, 1H), 7.33 (t, J = 7.6 Hz, 2H), 4.11 (s, 1H), 3.96 (s, 1H), 3.80 (dd, J = 14.8, 6.9 Hz, 1H), 3.74-3.59 (m, 2H), 2.02-1.91 (m, 1H), 1.91-1.75 (m, 2H), 1.63-1.51 (m, 1H) |
| 97 | 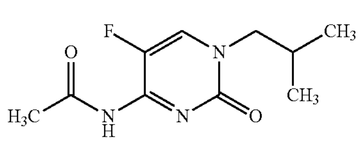 [SMILES: CC(=O)Nc1nc(=O)n(CC(C)C)cc1F] | white solid | 134.5-136.5 | ESIMS m/z 228 ([M + H]$^+$) | (CDCl$_3$) 7.72 (s, 1H), 7.43 (d, J = 4.6 Hz, 1H), 3.63 (d, J = 7.4 Hz, 3H), 2.67 (s, 3H), 2.29-2.12 (m, 1H), 0.98 (d, J = 6.7 Hz, 6H) |

TABLE I-continued

Compounds and Related Characterization Data

| Cmpd | Structure | Appearance | mp (° C.) | MS | $^1$H NMR$^a$ ($\delta$, solvent) |
|---|---|---|---|---|---|
| 98 | 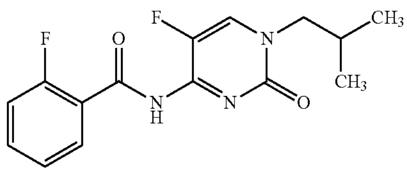 [SMILES: CC(C)Cn1cc(F)c(NC(=O)c2ccccc2F)nc1=O] | white solid | 161.3-163 | ESIMS m/z 308 ([M + H]$^+$) | (DMSO-d$_6$) 11.20 (s, 1H), 8.49 (s, 1H), 7.80-7.54 (m, 2H), 7.33 (t, J = 7.5 Hz, 2H), 3.62 (d, J = 6.5 Hz, 2H), 2.08 (s, 1H), 0.87 (d, J = 6.7 Hz, 6H) |
| 99 | 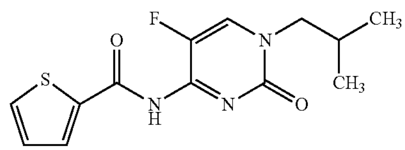 [SMILES: CC(C)Cn1cc(F)c(NC(=O)c2cccs2)nc1=O] | pale yellow solid | 125.6-127.5 | ESIMS m/z 296 ([M + H]$^+$) | (CDCl$_3$) 12.85 (s, 1H), 7.97 (dd, J = 3.8, 1.2 Hz, 1H), 7.61 (dd, J = 4.9, 1.2 Hz, 1H), 7.33 (d, J = 5.4 Hz, 1H), 7.14 (dd, J = 4.9, 3.8 Hz, 1H), 3.57 (d, 7 = 7.5 Hz, 2H), 2.19-2.04 (m, 1H), 0.99 (d, J = 6.7 Hz, 6H) |
| 100 | 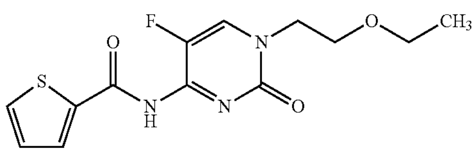 [SMILES: CCOCCn1cc(F)c(NC(=O)c2cccs2)nc1=O] | off-white solid | 109-110.4 | ESIMS m/z 312 ([M + H]$^+$), | (CDCl$_3$) 8.00-7.93 (m, 1H), 7.60 (dd, J = 4.8, 0.8 Hz, 1H), 7.56 (d, J = 5.6 Hz, 1H), 7.13 (dd, J = 4.7, 4.0 Hz, 1H), 3.98-3.90 (m, 2H), 3.70-3.63 (m, 2H), 3.51 (q, J = 7.0 Hz, 2H), 1.19 (t, J = 7.0 Hz, 3H) |
| 101 | 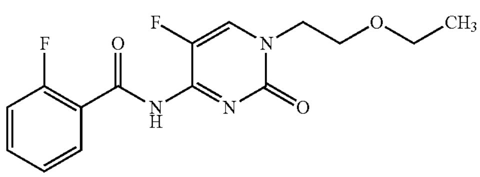 [SMILES: CCOCCn1cc(F)c(NC(=O)c2ccccc2F)nc1=O] | off-white solid | 116.8-117.8 | ESIMS m/z 324 ([M + H]$^+$) | (CDCl$_3$) 8.20 (td, J = 7.8, 1.6 Hz, 1H), 8.02 (t, J = 7.6 Hz, 1H), 7.69 (d, J = 5.5 Hz, 1H), 7.55 (dd, J = 13.1, 5.9 Hz, 1H), 7.32-7.24 (m, 1H), 7.18 (dd, J = 11.7, 8.3 Hz, 1H), 4.05-3.97 (m, 2H), 3.74-3.66 (m, 2H), 3.50 (q, J = 7.0 Hz, 2H), 1.19 (t, J = 7.0 Hz, 3H) |
| 103 | 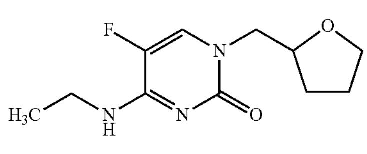 [SMILES: CCNc1nc(=O)n(CC2CCCO2)cc1F] | brown gum | | ESIMS m/z 242 ([M + H]$^+$) | (Acetone-$_6$) 7.61 (d, J = 6.9 Hz, 1H), 7.05-6.84 (m, 1H), 4.15-4.06 (m, 1H), 3.97 (dd, J = 13.7, 3.2 Hz, 1H), 3.83 (dd, J = 14.9, 6.7 Hz, 1H), 3.68 (dd, J = 14.8, 6.9 Hz, 1H), 3.51 (ddd, J = 20.0, 13.7, 7.3 Hz, 3H), 2.03-1.93 (m, 1H), 1.92-1.78 (m, 2H), 1.60 (dd, J = 12.1, 8.1 Hz, 1H), 1.20 (t, J = 7.2 Hz, 3H) |

TABLE I-continued

Compounds and Related Characterization Data

| Cmpd | Structure | Appearance | mp (° C.) | MS | $^1$H NMR$^a$ (δ, solvent) |
|---|---|---|---|---|---|
| 104 | 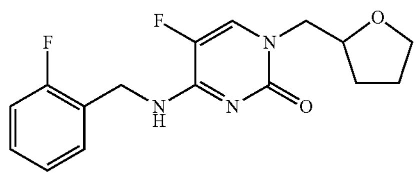 [SMILES: O=c1nc(NCc2ccccc2F)c(F)cn1CC1CCCO1] | gum | | ESIMS m/z 322 ([M + H]$^+$) | (Acetone-$d_6$) 7.70 (d, J = 6.7 Hz, 1H), 7.53-7.42 (m, J = 6.9 Hz, 2H), 7.37-7.27 (m, 1H), 7.21-7.06 (m, 2H), 4.75 (d, J = 5.7 Hz, 2H), 4.11 (qd, J = 7.1, 3.2 Hz, 1H), 3.99 (dd, J = 13.6, 3.2 Hz, 1H), 3.88-3.79 (m, 1H), 3.69 (dd, J = 14.9, 6.9 Hz, 1H), 3.55 (dd, J = 13.6, 7.8 Hz, 1H), 2.03-1.93 (m, 1H), 1.92-1.80 (m, 2H), 1.67-1.53 (m, 1H) |
| 106 | 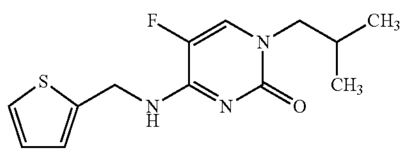 [SMILES: CC(C)Cn1cc(F)c(NCc2cccs2)nc1=O] | Off-white solid | 88.8-91.7 | ESIMS m/z 282 ([M + H]$^+$) | (CDCl$_3$) 7.30-7.25 (m, 2H), 7.19 (d, J = 5.8 Hz, 1H), 7.08 (d, J = 3.1 Hz, 1H), 6.99 (dd, J = 5.1, 3.5 Hz, 1H), 4.91 (d, J = 4.9 Hz, 2H), 3.57 (d, J = 7.5 Hz, 2H), 2.17 (dt, J = 13.6, 6.8 Hz, 1H), 0.96 (d, J = 6.7 Hz, 6H) |
| 107 | 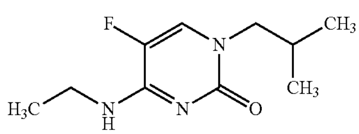 | brown gum | | ESIMS m/z 214 ([M + H]$^+$) | (CDCl$_3$) 7.14 (d, J = 5.9 Hz, 1H), 3.65-3.50 (m, 4H), 2.16 (dt, J = 13.7, 6.9 Hz, 1H), 1.27 (t, J = 7.3 Hz, 3H), 0.94 (d, J = 6.7 Hz, 6H) |
| 108 | 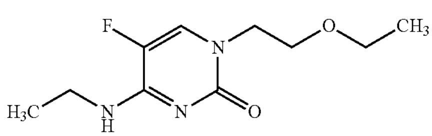 [SMILES: CCNc1nc(=O)n(CCOCC)cc1F] | brown solid | 63-65 | ESIMS m/z 230 ([M + H]$^+$) | (Acetone-$d_6$) 7.61 (d, J = 6.8 Hz, 1H), 6.99 (s, 1H), 3.85 (t, J = 5.2 Hz, 2H), 3.62 (t, J = 5.2 Hz, 2H), 3.54-3.42 (m, 4H), 1.20 (t, J = 7.2 Hz, 3H), 1.12 (t, J = 7.0 Hz, 3H) |
| 109 | 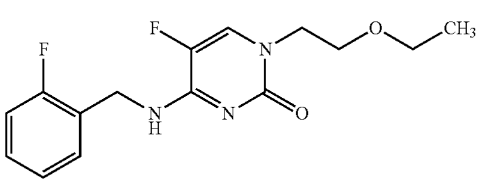 [SMILES: CCOCCn1cc(F)c(NCc2ccccc2F)nc1=O] | brown gum | | ESIMS m/z 310 ([M + H]$^+$) | (Acetone-$d_6$) 7.69 (d, J = 6.7 Hz, 1H), 7.48 (t, J = 7.0 Hz, 1H), 7.37-7.27 (m, 1H), 7.20-7.05 (m, 2H), 4.75 (d, J = 5.5 Hz, 2H), 3.88 (dd, J = 11.8, 6.6 Hz, 2H), 3.61 (dd, 7 = 12.7, 7.7 Hz, 2H), 3.54-3.41 (m, 2H), 1.18-1.05 (m, 3H) |

TABLE I-continued

Compounds and Related Characterization Data

| Cmpd | Structure | Appearance | mp (° C.) | MS | $^1$H NMR$^a$ (δ, solvent) |
|---|---|---|---|---|---|
| 110 | (structure) | gum | | ESIMS m/z 298 ([M + H]$^+$) | (Acetone-d$_6$) 7.68 (d, J = 6.7 Hz, 1H), 7.57 (s, 1H), 7.32 (dd, J = 5.1, 1.2 Hz, 1H), 7.12-7.04 (m, 1H), 6.95 (dd, J = 5.1, 3.5 Hz, 1H), 4.85 (d, J = 5.9 Hz, 2H), 3.88 (t, J = 5.2 Hz, 2H), 3.63 (t, J = 5.2 Hz, 2H), 3.47 (q, J = 7.0 Hz, 2H), 1.12 (t, J = 7.0 Hz, 3H) |

Example 26

Evaluation of Fungicidal Activity: Leaf Blotch of Wheat (*Mycosphaerella graminicola*; anamorph: *Septoria tritici*; Bayer code SEPTTR)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber) to permit spores to germinate and infect the leaf. The plants were then transferred to a greenhouse for disease to develop.

The following table presents the activity of typical compounds of the present disclosure when evaluated in these experiments. The effectiveness of the test compounds in controlling disease was determined by assessing the severity of disease on treated plants, then converting the severity to percent control based on the level of disease on untreated, inoculated plants.

In each case of Table II the rating scale is as follows:

| % Disease Control | Rating |
|---|---|
| 76-100 | A |
| 51-75 | B |
| 26-50 | C |
| 0-25 | D |
| Not Tested | E |

TABLE II

One-Day Protectant (1DP) and Three-Day Curative (3DC) Activity of Compounds on SEPTTR at 100 ppm

| Cmpd | SEPTTR 100 PPM 1DP | SEPTTR 100 PPM 3DC |
|---|---|---|
| 1 | A | A |
| 2 | A | A |
| 3 | A | A |
| 4 | C | D |
| 5 | D | D |
| 6 | D | D |
| 7 | D | D |
| 8 | C | D |
| 9 | C | D |
| 10 | C | B |
| 11 | C | D |
| 12 | A | A |
| 13 | A | A |
| 14 | D | D |
| 15 | D | D |
| 16 | D | D |
| 17 | B | A |
| 18 | C | B |
| 19 | C | D |
| 20 | D | D |
| 21 | A | A |
| 22 | A | A |
| 23 | A | A |
| 24 | A | A |
| 25 | D | D |
| 26 | D | C |
| 27 | D | D |
| 28 | B | A |
| 29 | B | A |
| 30 | D | A |
| 31 | D | A |
| 32 | A | A |
| 33 | D | B |
| 34 | A | A |
| 35 | B | B |
| 36 | B | C |
| 37 | D | D |
| 38 | D | D |
| 39 | D | A |
| 40 | D | D |
| 41 | A | A |
| 42 | E | E |
| 43 | C | D |
| 44 | E | E |
| 45 | E | E |
| 46 | D | D |
| 47 | C | D |
| 48 | E | E |
| 49 | E | E |
| 50 | E | E |
| 51 | E | E |
| 52 | E | E |
| 53 | E | E |
| 54 | E | E |
| 55 | E | E |

TABLE II-continued

One-Day Protectant (1DP) and Three-Day Curative (3DC) Activity of Compounds on SEPTTR at 100 ppm

| Cmpd | SEPTTR 100 PPM 1DP | SEPTTR 100 PPM 3DC |
|---|---|---|
| 56 | C | B |
| 57 | D | D |
| 58 | A | A |
| 59 | E | E |
| 60 | E | E |
| 61 | E | E |
| 62 | E | E |
| 63 | E | E |
| 64 | E | E |
| 65 | D | D |
| 66 | D | D |
| 67 | D | B |
| 68 | E | E |
| 69 | E | E |
| 70 | E | E |
| 71 | E | E |
| 72 | E | E |
| 73 | E | E |
| 74 | A | B |
| 75 | C | A |
| 76 | D | B |
| 77 | C | D |
| 78 | E | E |
| 79 | E | E |
| 80 | D | B |
| 81 | C | A |
| 82 | C | C |
| 83 | C | C |
| 84 | E | E |
| 85 | D | D |
| 86 | C | C |
| 87 | D | B |
| 88 | D | B |
| 89 | D | C |
| 90 | D | D |
| 91 | D | D |
| 92 | A | A |
| 93 | D | B |
| 94 | D | D |
| 95 | D | B |
| 96 | D | C |
| 97 | C | C |
| 98 | D | D |
| 99 | D | A |
| 100 | E | E |
| 101 | E | E |
| 102 | E | E |
| 103 | E | E |
| 104 | E | E |
| 105 | D | C |
| 106 | C | C |
| 107 | D | C |
| 108 | E | E |
| 109 | E | E |
| 110 | E | E |

What is claimed is:

1. A method for the control and prevention of fungal attack on a plant, the method including the steps of:

applying a fungicidally effective amount of at least one of the compounds of Formula 1 to at least one of the plant, an area adjacent to the plant, soil adapted to support growth of the plant, a root of the plant, foliage of the plant, and a seed adapted to produce the plant;

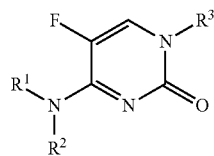

Formula I wherein $R^1$ is:
  H
  $C_1$-$C_6$ alkyl optionally substituted with 1-3 $R^4$;
  $C_1$-$C_6$ alkenyl optionally substituted with 1-3 $R^4$;
  $C_3$-$C_6$ alkenyl optionally substituted with 1-3 $R^4$;
  substituted phenyl, substituted benzyl, phenyl or benzyl wherein substituents for the substituted phenyl or the substituted benzyl are selected from the group consisting of: 1-3 $R^5$, a 5- or 6-membered saturated or unsaturated ring system, a 5-6 fused ring system, or a 6-6 fused ring system each containing 1-3 heteroatoms wherein each ring may be optionally substituted with 1-3 $R^5$, biphenyl or naphthyl optionally substituted with 1-3 $R^5$;
  —(CHR6)$_m$OR$^7$;
  —(CHR6)$_m$N(R9)R$^{10}$;
  —C(=O)R$^8$;
  —C(=S)R$^8$;
  —S(O)$_2$R$^8$;
  —C(=O)OR$^8$;
  —C(=S)OR$^8$;
  —(CHR6)$_m$N(R$^9$)R$^{10}$;
  —C(=O)N(R$^9$)R$^{10}$; or
  —C(=S)N(R$^9$)R$^{10}$;
wherein m is an integer 1-4;
$R^2$ is:
  H; or
  $C_1$-$C_6$ alkyl optionally substituted with $R^4$;
alternatively $R^1$ and $R^2$ may be taken together to form:
  =CR$^{11}$N(R$^{12}$)R$^{13}$;
$R^3$ is:
  $C_1$-$C_6$ branched or unbranched linear alkyl optionally substituted with 1-3 $R^4$, $C_1$-$C_6$ haloalkyl, $C_1$-$C_6$ hydroxyalkyl, $C_2$-$C_6$ alkoxyalkyl, $C_2$-$C_6$ haloalkoxyalkyl, $C_2$-$C_6$ alkenyl optionally substituted with $R^{14}$, $C_2$-$C_6$ haloalkenyl, $C_3$-$C_6$ alkenyl, substituted phenyl, substituted benzyl, phenyl or benzyl wherein substituents for the substituted phenyl or the substituted benzyl are selected from the group consisting of: 1-3 $R^5$, a 5- or 6-membered saturated or unsaturated ring system, a 5-6 fused ring system, or a 6-6 fused ring system each containing 1-3 heteroatoms wherein each ring may be optionally substituted with 1-3 $R^5$, biphenyl or naphthyl optionally substituted with 1-3 $R^5$;
  —(CHR$^6$)$_m$OR$^7$;
  —(CHR$^6$)$_m$SR$^8$; or
  —(CHR$^6$)$_m$N(R$^9$)R$_{10}$;
with the proviso that if $R^3$ is CH$_3$, then $R^1$ and $R^2$ are not both H or both CH$_3$ and the combination of $R^1$ and $R^2$ is not H and CH$_3$; $R^4$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, halothio, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, $C_3$-$C_6$ trialkylsilyl, phenyl optionally substituted with 1-3 $R^5$, or with a 5- or 6-membered saturated or unsaturated ring containing 1-3 heteroatoms wherein each ring may be optionally substituted with 1-3 $R^5$;

$R^5$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, halothio, amino, $C_1$-$C_6$ alkylamino, $C_2$-$C_6$ dialkylamino, $C_2$-$C_6$ alkoxycarbonyl, $C_2$-$C_6$ alkylcarbonyl, $C_1$-$C_6$ alkylsulfonyl, nitro, hydroxyl, or cyano;

$R^6$ is H, $C_1$-$C_6$ alkyl, $C_1$-$C_6$ alkoxy, $C_1$-$C_6$ alkoxycarbonyl, phenyl or benzyl wherein each of the phenyl or the benzyl may be optionally substituted with 1-3 $R^5$;

$R^7$ is H, $C_1$-$C_8$ alkyl, $C_2$-$C_6$ alkenyl, $C_3$-$C_6$ alkynyl, $C_1$-$C_6$ haloalkyl, $C_1$-$C_6$ alkoxyalkyl, $C_2$-$C_6$ trialkylsilyl, $C_2$-$C_6$ trialkylsilylalkyl $C_2$-$C_6$ alkylcarbonyl, $C_1$-$C_6$ alkoxycarbonyl, substituted phenyl, substituted benzyl, phenyl or benzyl wherein substituents for the substituted phenyl or the substituted benzyl are selected from the group consisting of: 1-3 $R^5$, a 5- or 6-membered saturated or unsaturated ring system, a 5-6 fused ring system, or a 6-6 fused ring system each containing 1-3 heteroatoms wherein each ring may be optionally substituted with 1-3 $R^5$, biphenyl or naphthyl optionally substituted with 1-3 $R^5$;

$R^8$ is H, $C_1$-$C_6$ alkyl, C2-$C_6$ alkenyl, C3-$C_6$ alkynyl, $C_1$-$C_6$ haloalkyl, $C_1$-$C_6$ alkoxyalkyl, substituted phenyl, substituted benzyl, phenyl or benzyl wherein substituents for the substituted phenyl or the substituted benzyl are selected from the group consisting of: 1-3 $R^5$, a 5- or 6-membered saturated or unsaturated ring system, a 5-6 fused ring system, or a 6-6 fused ring system each containing 1-3 heteroatoms wherein each ring may be optionally substituted with 1-3 $R^5$, biphenyl or naphthyl optionally substituted with 1-3 $R^5$;

$R^9$ is H $C_1$-$C_6$ alkyl, $C_1$-$C_6$ haloalkyl, $C_1$-$C_6$ alkoxyalkyl, $C_2$-$C_6$ alkylcarbonyl, substituted phenyl, substituted benzyl, phenyl or benzyl wherein substituents for the substituted phenyl or the substituted benzyl are selected from the group consisting of: 1-3 $R^5$, a 5- or 6-membered saturated or unsaturated ring system, a 5-6 fused ring system, or a 6-6 fused ring system each containing 1-3 heteroatoms wherein each ring may be optionally substituted with 1-3 $R^5$, biphenyl or naphthyl optionally substituted with 1-3 $R^5$;

$R^{10}$ is H, $C_1$-$C_6$ alkyl, $C_1$-$C_6$ haloalkyl, $C_1$-$C_6$ alkoxyalkyl, $C_2$-$C_6$ alkylcarbonyl, or benzyl, wherein the benzyl may be optionally substituted with 1-3 $R^5$;

alternatively $R^9$ and $R^{10}$ may be taken together to form a 5- or 6-membered saturated or unsaturated ring containing 1-3 heteroatoms wherein each ring may be optionally substituted with 1-3 $R^5$;

$R^{11}$ is H or $C_1$-$C_4$ alkyl;

$R^{12}$ is H, cyano, hydroxyl, $C_1$-$C_4$ alkyl, $C_1$-$C_6$ alkoxy, $C_2$-$C_6$, alkylcarbonyl, phenyl or benzyl wherein each of the phenyl or the benzyl may be optionally substituted with 1-3 $R^5$; a 5- or 6-membered saturated or unsaturated ring system, a 5-6 fused ring system, or a 6-6 fused ring system each containing 1-3 heteroatoms wherein each ring may be optionally substituted with 1-3 $R^5$, biphenyl or naphthyl optionally substituted with 1-3 $R^5$;

alternatively $R^{11}$ and $R^{12}$ may be taken together to form a 5- or 6-membered saturated or unsaturated ring containing 1-3 heteroatoms wherein each ring may be optionally substituted with 1-3 $R^5$;

$R^{13}$ is H, $C_1$-$C_4$ alkyl, $C_1$-$C_6$ alkoxy, $C_2$-$C_6$, alkylcarbonyl, phenyl or benzyl wherein each of the phenyl or the benzyl may be optionally substituted with 1-3 $R^5$; a 5- or 6-membered saturated or unsaturated ring system, a 5-6 fused ring system, or a 6-6 fused ring system each containing 1-3 heteroatoms wherein each ring may be optionally substituted with 1-3 $R^5$, biphenyl or naphthyl optionally substituted with 1-3 $R^5$; and alternatively $R^{12}$ and $R^{13}$ may be taken together to form a 5- or 6-membered saturated or unsaturated ring containing 1-3 heteroatoms wherein each ring may be optionally substituted with 1-3 $R^5$;

$R^{14}$ is phenyl or benzyl wherein each of the phenyl or the benzyl may be optionally substituted with 1-3 $R^5$.

2. The method of claim 1, wherein said applying includes applying a composition including the compound of Formula I and a phytologically acceptable carrier material.

3. The method of claim 1, wherein the fungal attack includes a fungal pathogen selected from the group consisting of: Apple Scab (*Venturia inaequalis*), Leaf Blotch of Wheat (*Septoria tritici*), Leaf Spot of Sugarbeets (*Cercospora beticola*), Leaf Spots of Peanut (*Cercospora arachidicola and Cercosporidium personatum*), and Black Sigatoka of Banana (*Mycosphaerella fijiensis*).

4. The method of claim 1, wherein:
$R^1$ is —(CHR$^6$)$_m$N(R$^9$)(R$^{10}$);
$R^2$ is H or methyl;
$R^3$ is —(CHR$^6$)$_m$N(R$^9$)(R$^{10}$);
m is 1; and
$R^9$ and $R^{10}$ are independently H, or methyl.

5. The method of claim 1, wherein the compound is:

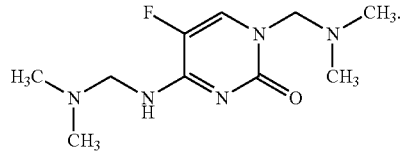 [SMILES: CN(C)CNc1nc(=O)n(CN(C)C)cc1F]

6. The method of claim 1, wherein $R^3$ is selected from the group consisting of:
—CH$_2$N(CH$_3$)$_2$, —CH$_2$-(4-methyl 1-piperazinyl), and —CH$_2$-(4-morphonlinyl).

7. The method of claim 4, wherein $R^1$ is selected from the group consisting of:
—CH$_2$N(CH$_3$)$_2$, —CH$_2$-(4-methyl 1-piperazinyl), and —CH$_2$-(4-morphonlinyl); and $R^2$ is H.

8. The method of claim 1, wherein the compound is selected from the group consisting of:

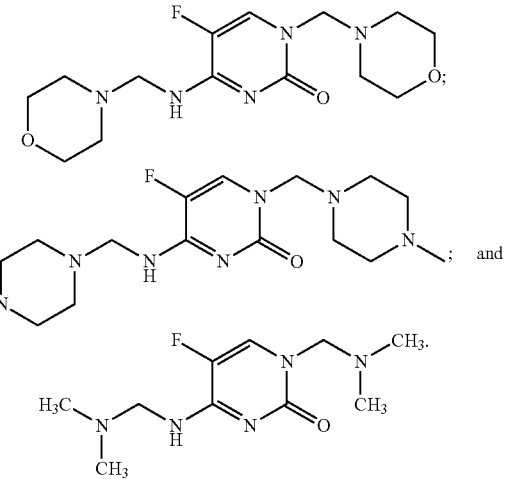

9. The method of claim 1, wherein:
$R^1$ is: H;
$R^2$ is H;
$R^3$ is —$(CHR^6)_m OR^7$, $C_2$-$C_6$ alkenyl, cyclopropylmethyl, or (tetrahydrofuran-2-yl)methyl,
wherein m is an integer 1-4;
$R^5$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, halothio, amino, $C_1$-$C_6$ alkylamino, $C_2$-$C_6$ dialkylamino, $C_2$-$C_6$ alkoxycarbonyl, $C_2$-$C_6$ alkylcarbonyl, $C_1$-$C_6$ alkylsulfonyl, nitro, hydroxyl, or cyano;
$R^6$ is H, $C_1$-$C_6$ alkyl, $C_1$-$C_6$ alkoxy, $C_1$-$C_6$ alkoxycarbonyl, phenyl or benzyl wherein each of the phenyl or the benzyl may be optionally substituted with 1-3 $R^5$; and
$R^7$ is H, $C_1$-$C_8$ alkyl, $C_2$-$C_6$ alkenyl, $C_3$-$C_6$ alkynyl, $C_1$-$C_6$ haloalkyl, $C_1$-$C_6$ alkoxyalkyl, $C_2$-$C_6$ trialkylsilyl, $C_2$-$C_6$ trialkylsilylalkyl $C_2$-$C_6$ alkylcarbonyl, $C_1$-$C_6$ alkoxycarbonyl, benzyl, phenyl or benzyl wherein each of the phenyl or the benzyl may be optionally substituted with 1-3 $R^5$, or with a 5- or 6-membered saturated or unsaturated ring system, or with a 5-6 fused ring system, or with a 6-6 fused ring system each containing 1-3 heteroatoms wherein each ring may be optionally substituted with 1-3 $R^5$, biphenyl or naphthyl optionally substituted with 1-3 $R^5$.

10. The method of claim 9, wherein m is 1.

11. The method of claim 9, wherein $R^3$ is selected from the group consisting of:

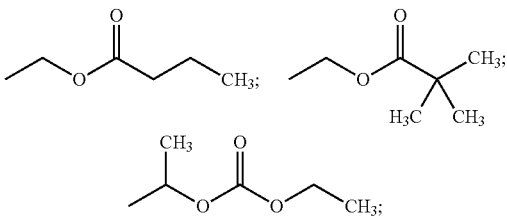

cyclopropylmethyl, and (tetrahydrofuran-2-yl)methyl.

* * * * *